US009480666B2

(12) United States Patent
Deuse et al.

(10) Patent No.: US 9,480,666 B2
(45) Date of Patent: Nov. 1, 2016

(54) COMPOSITIONS AND METHODS FOR INHIBITING INTIMAL HYPERPLASIA

(71) Applicants: Tobias Deuse, Hamburg (DE); Sonja Schrepfer, Hamburg (DE)

(72) Inventors: Tobias Deuse, Hamburg (DE); Sonja Schrepfer, Hamburg (DE)

(73) Assignees: Tobias Deuse, Hamburg (DE); Sonja Schrepfer, Hamburg (DE)

( * ) Notice: Subject to any disclaimer, the term of this patent is extended or adjusted under 35 U.S.C. 154(b) by 0 days.

(21) Appl. No.: 14/691,486

(22) Filed: Apr. 20, 2015

(65) Prior Publication Data

US 2016/0045464 A1    Feb. 18, 2016

Related U.S. Application Data

(60) Provisional application No. 62/038,206, filed on Aug. 16, 2014.

(51) Int. Cl.
*A61K 31/19*    (2006.01)
*A61K 9/08*    (2006.01)

(52) U.S. Cl.
CPC    *A61K 31/19* (2013.01); *A61K 9/08* (2013.01)

(58) Field of Classification Search
CPC ....... A61K 31/19; A61K 9/0053; A61K 9/08
USPC .......................................................... 514/557
See application file for complete search history.

(56) References Cited

U.S. PATENT DOCUMENTS

| | | | |
|---|---|---|---|
| 6,423,705 B1 | 7/2002 | Tracey et al. | |
| 8,609,724 B2 | 12/2013 | Michelakis et al. | |
| 2005/0079200 A1 | 4/2005 | Rathenow et al. | |
| 2006/0194878 A1* | 8/2006 | Lopaschuk | A61K 31/19 514/557 |
| 2009/0209618 A1 | 8/2009 | Dang et al. | |
| 2009/0280153 A1 | 11/2009 | Hunter et al. | |

OTHER PUBLICATIONS

Deuse et al , Dichloroacetate prevents restenosis in preclinical animal models of vessel injury, Nature, 2014, 509(7502),p. 641-644.*

* cited by examiner

*Primary Examiner* — T. Victor Oh
(74) *Attorney, Agent, or Firm* — William A. English; Vista IP Law Group LLP

(57) ABSTRACT

Methods are provided for preventing, inhibiting, or treating intimal hyperplasia in a patient who has undergone a coronary bypass procedure that include providing a solution comprising DCA added to water; and administering the solution orally to a patient to prevent, inhibit, or treat intimal hyperplasia.

18 Claims, 28 Drawing Sheets

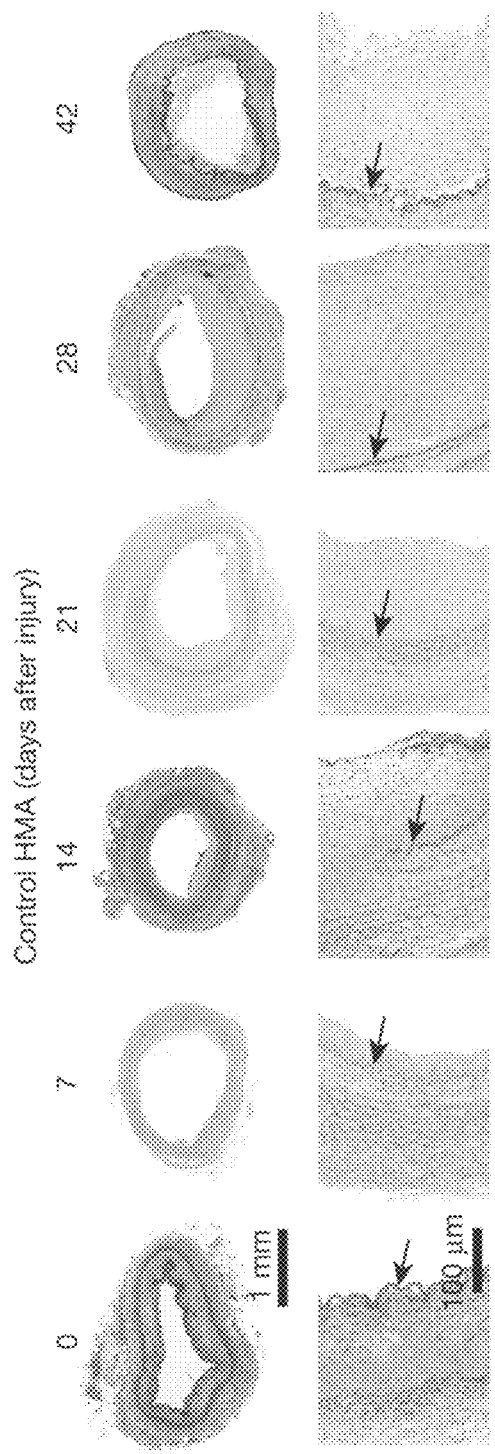

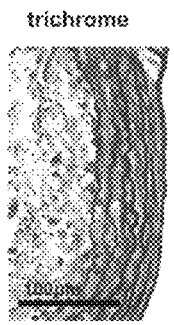
EXTENDED FIG. 1g
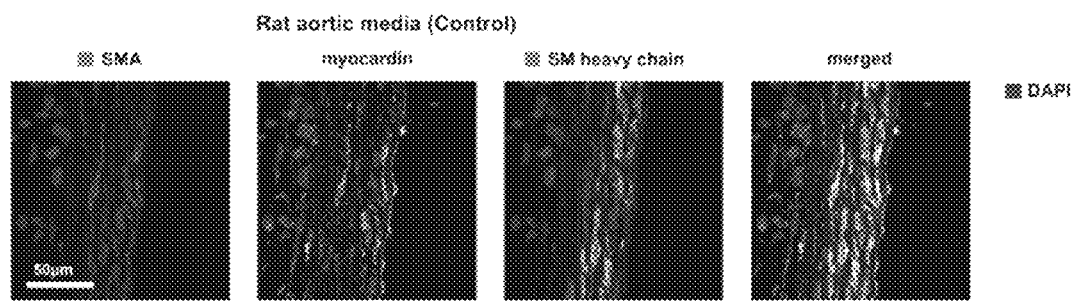
EXTENDED FIG. 1h
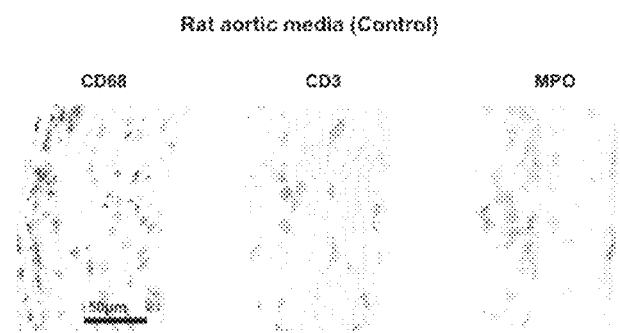
EXTENDED FIG. 1i

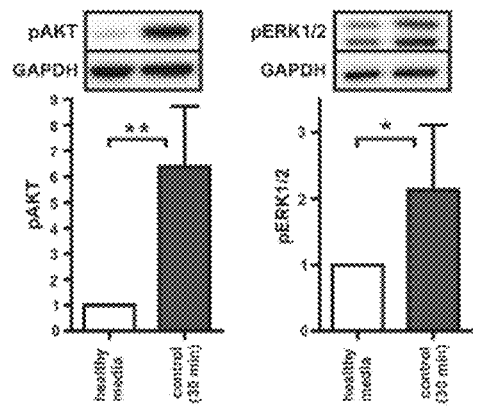
EXTENDED FIG. 1j
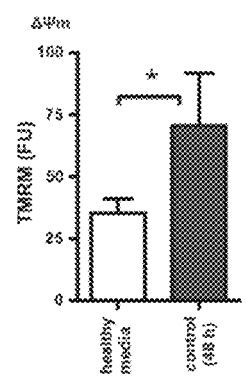
EXTENDED FIG. 1k
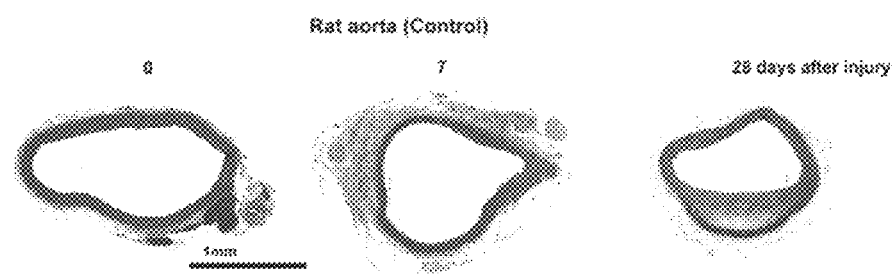
EXTENDED FIG. 1l

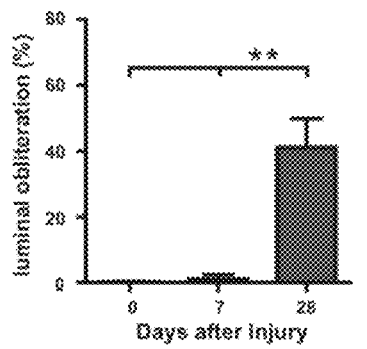
EXTENDED FIG. 1m
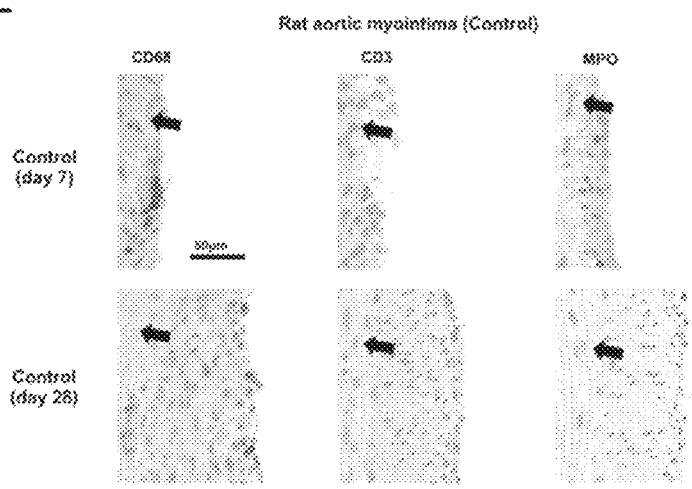
EXTENDED FIG. 1n
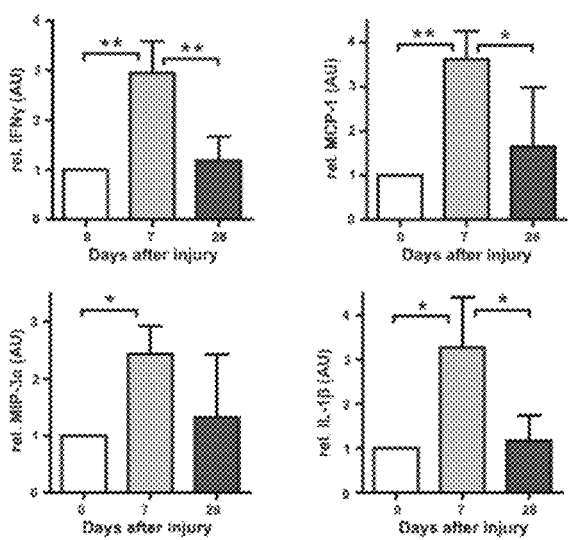
EXTENDED FIG. 1o

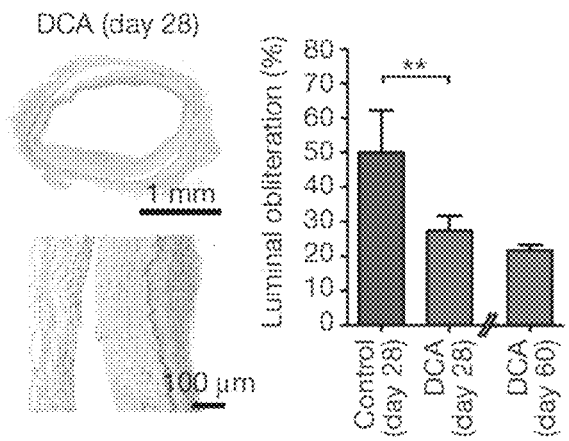
FIG. 2a
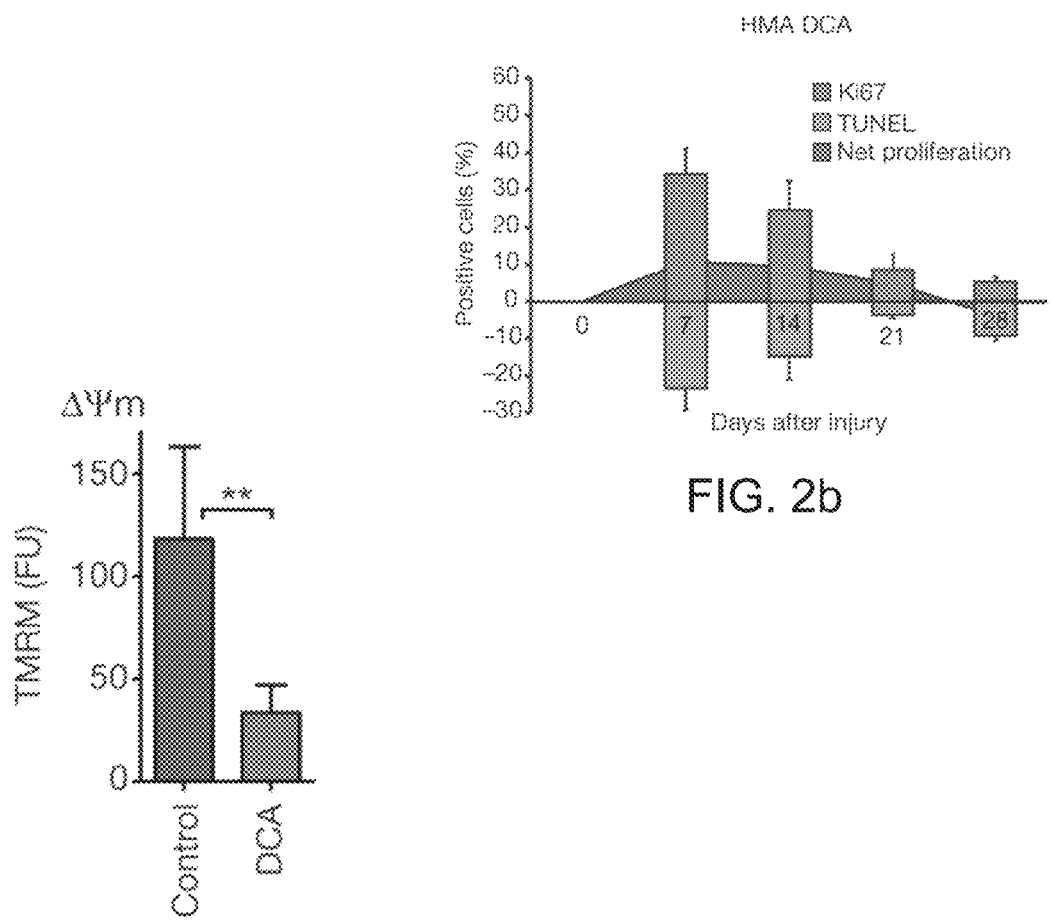
FIG. 2b
FIG. 2c

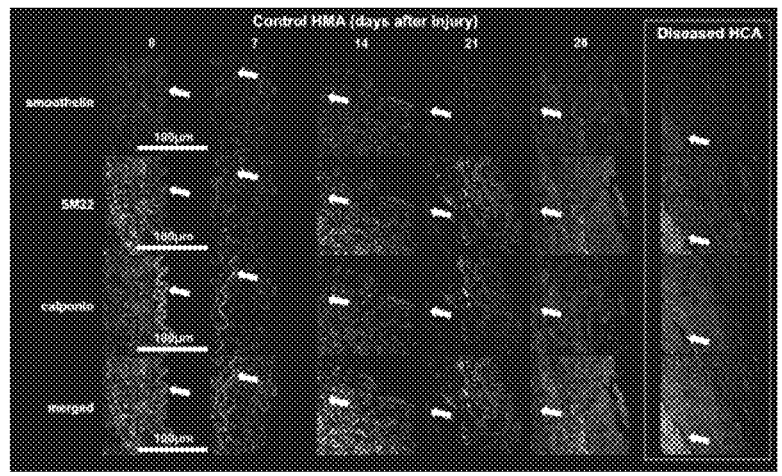
EXTENDED FIG. 2g
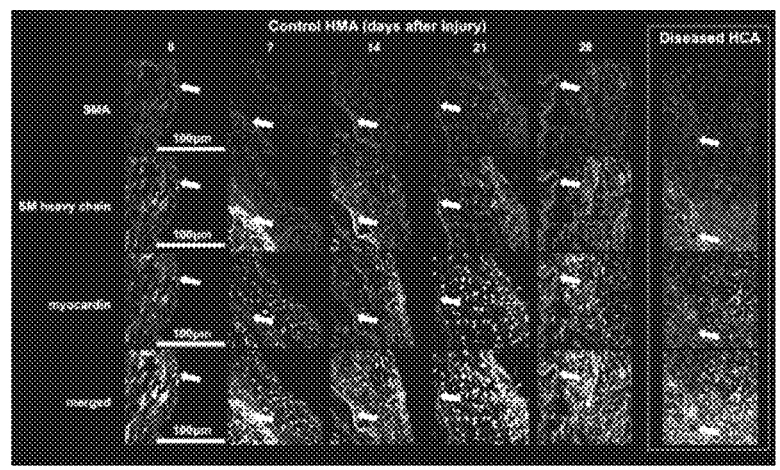
EXTENDED FIG. 2h
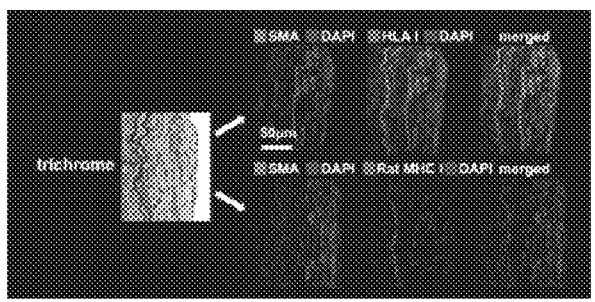
EXTENDED FIG. 2i

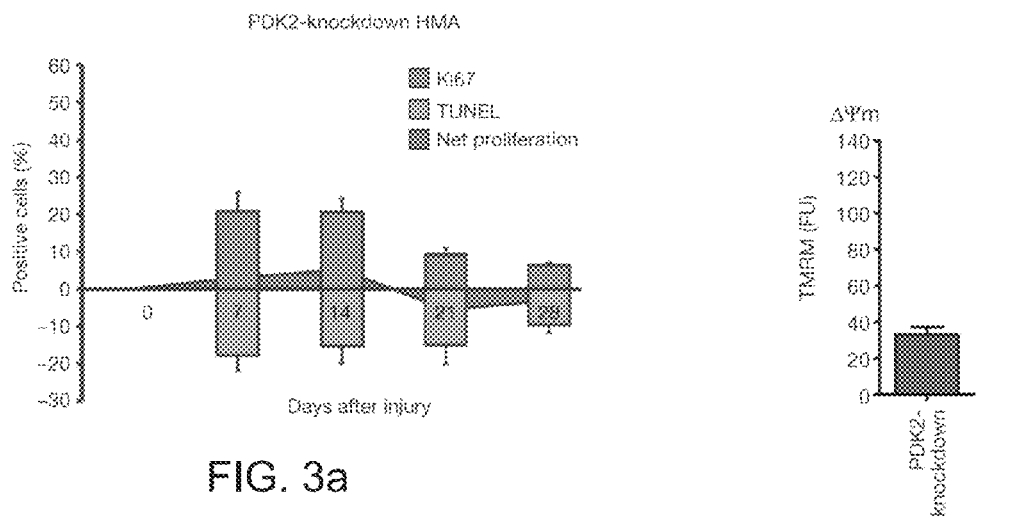
FIG. 3a
FIG. 3b
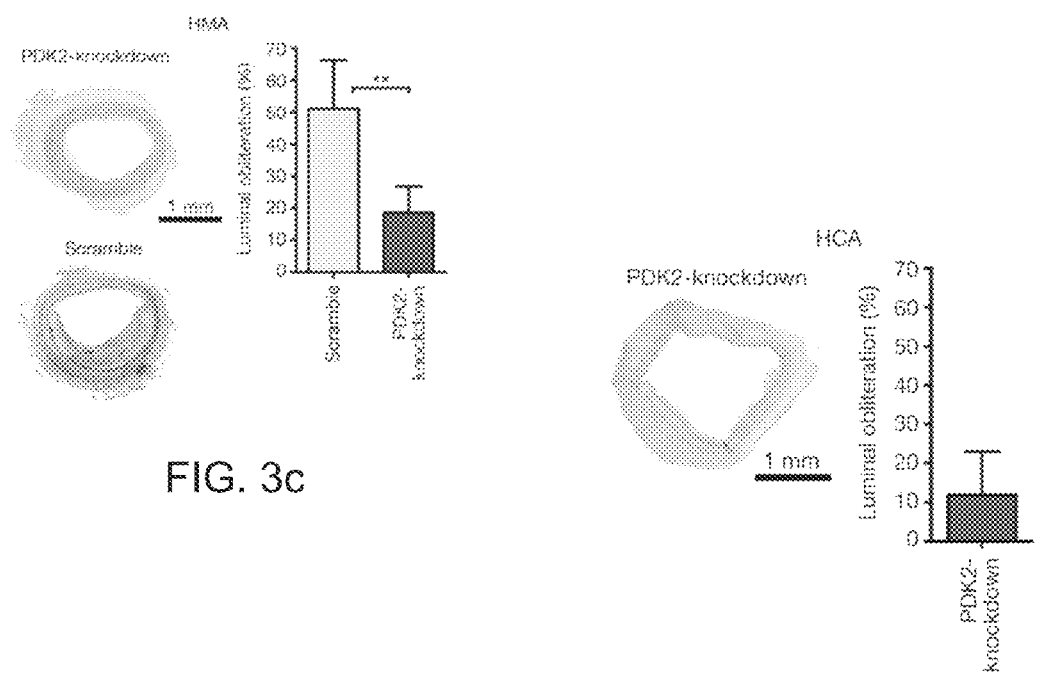
FIG. 3c
FIG. 3d

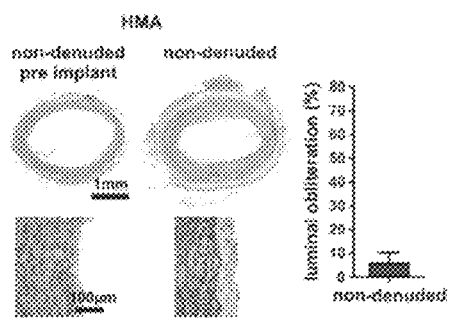
EXTENDED FIG. 3e
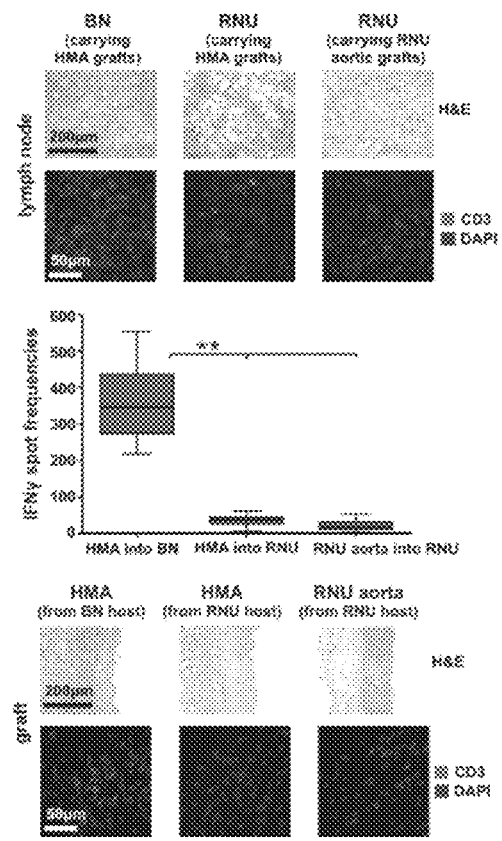
EXTENDED FIG. 3f
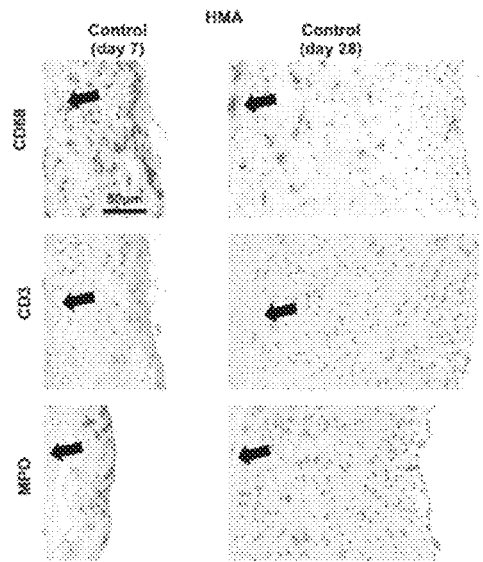
EXTENDED FIG. 3g

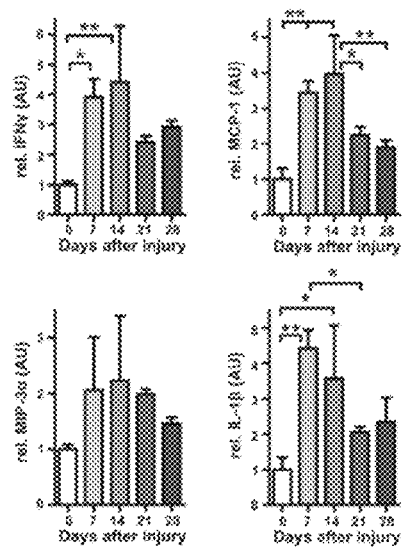
EXTENDED FIG. 3h
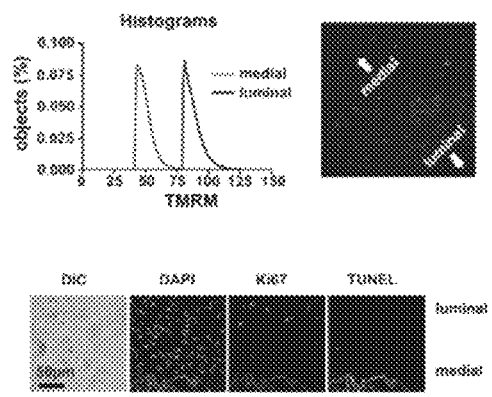
EXTENDED FIG. 3i
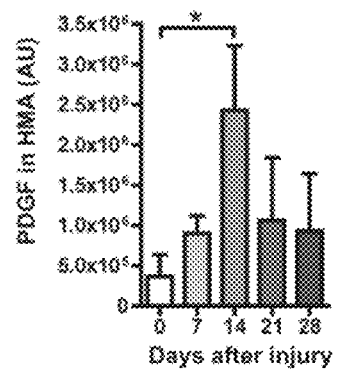
EXTENDED FIG. 3j
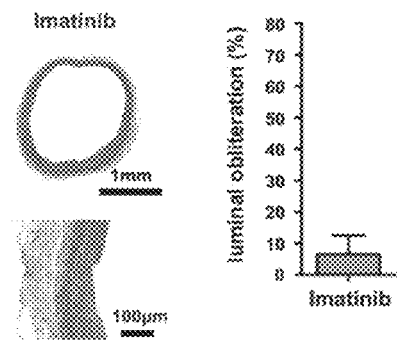
EXTENDED FIG. 3k

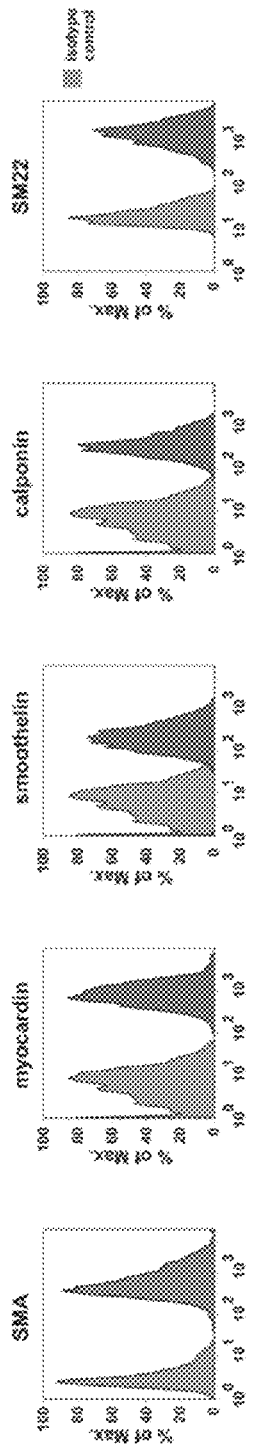
EXTENDED FIG. 4e
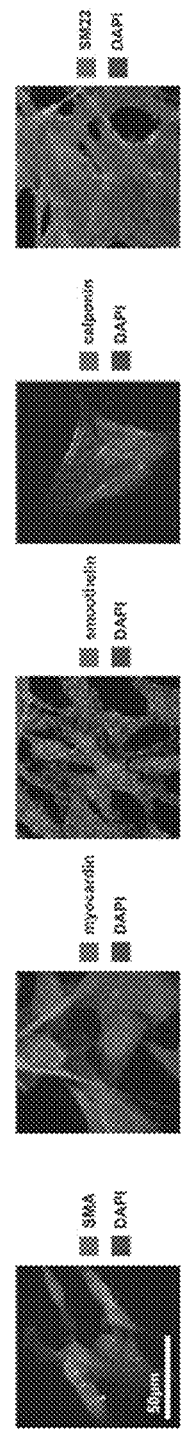
EXTENDED FIG. 4f

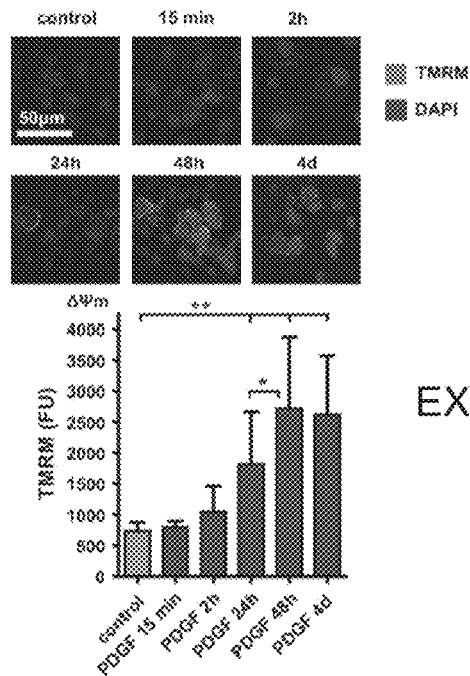
EXTENDED FIG. 4g
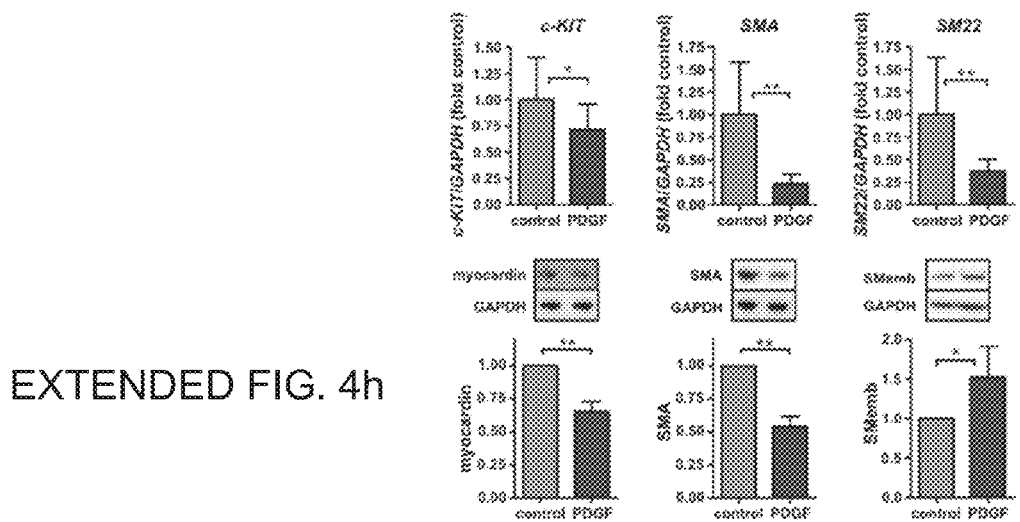
EXTENDED FIG. 4h

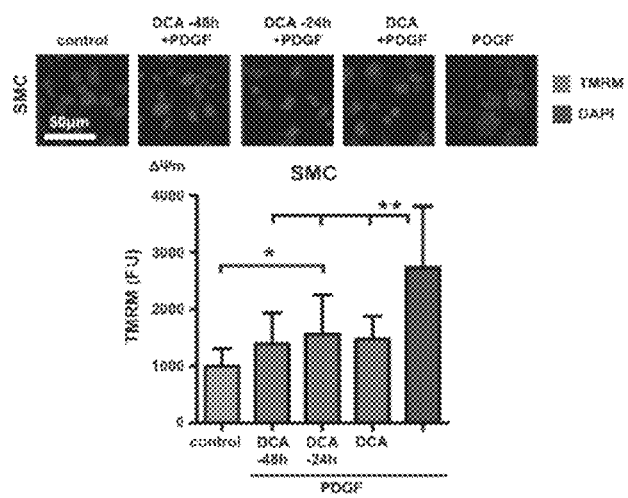
EXTENDED FIG. 5a
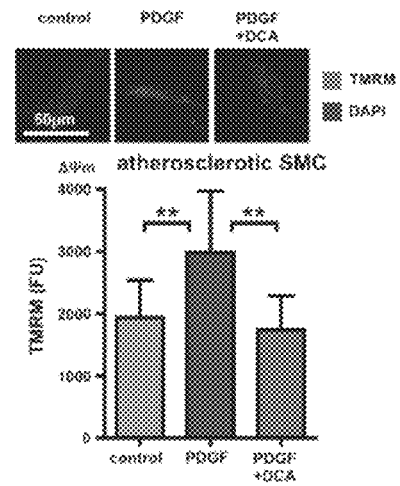
EXTENDED FIG. 5b
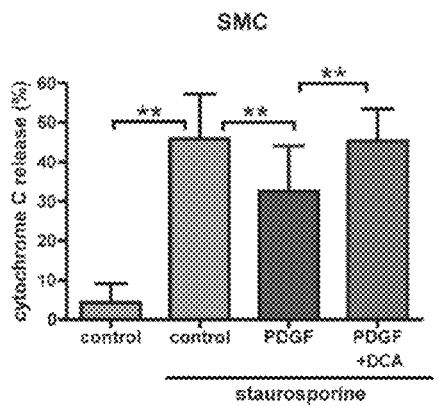
EXTENDED FIG. 5c

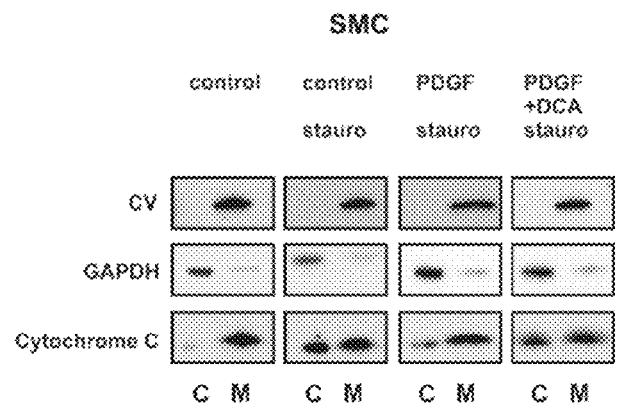
EXTENDED FIG. 5d
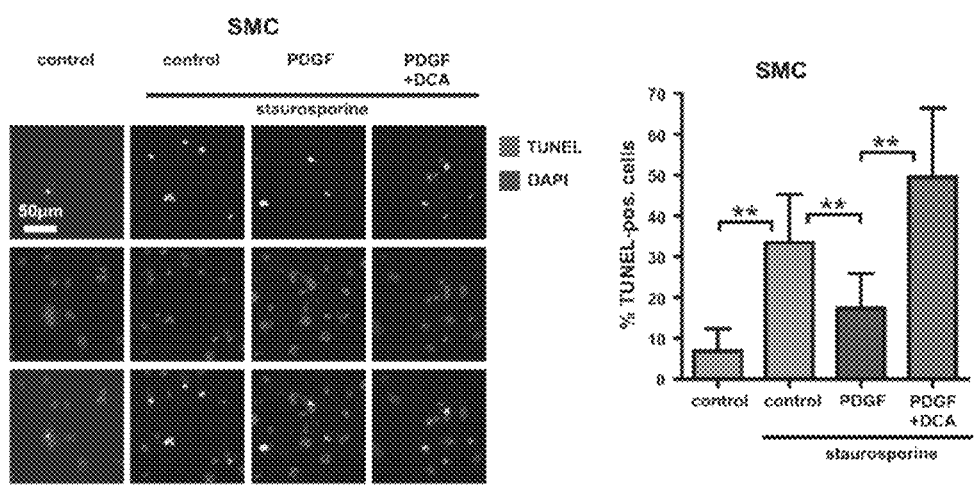
EXTENDED FIG. 5e

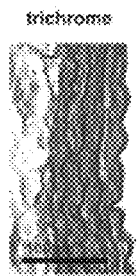
EXTENDED FIG. 6a
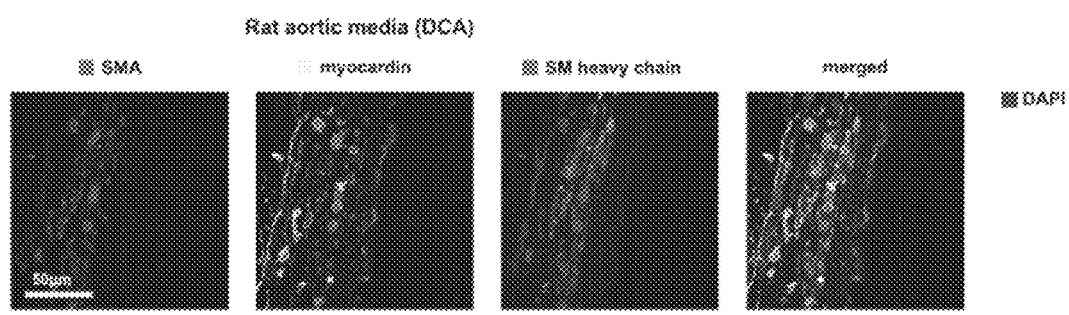
EXTENDED FIG. 6b
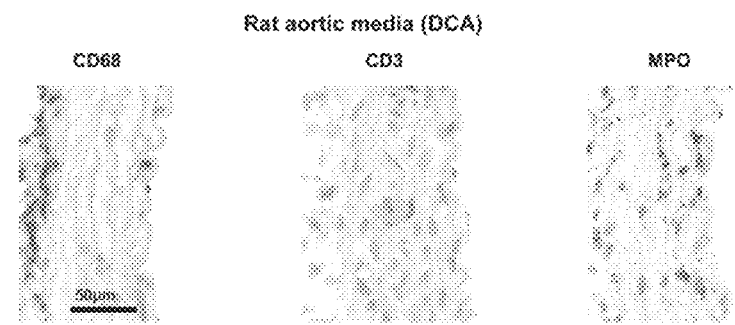
EXTENDED FIG. 6c

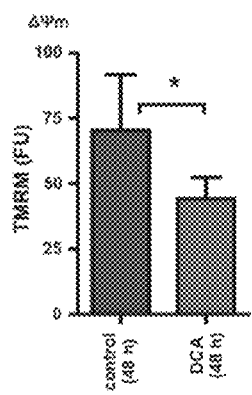
EXTENDED FIG. 6d
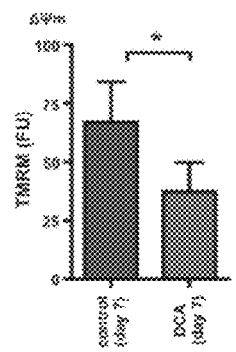
EXTENDED FIG. 6f
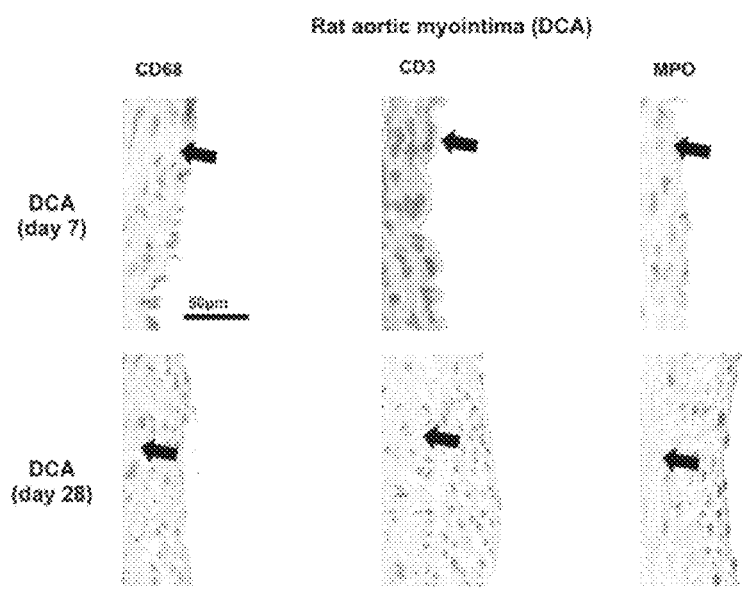
EXTENDED FIG. 6e

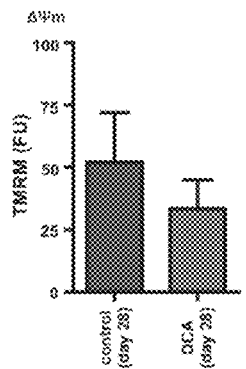
EXTENDED FIG. 6g
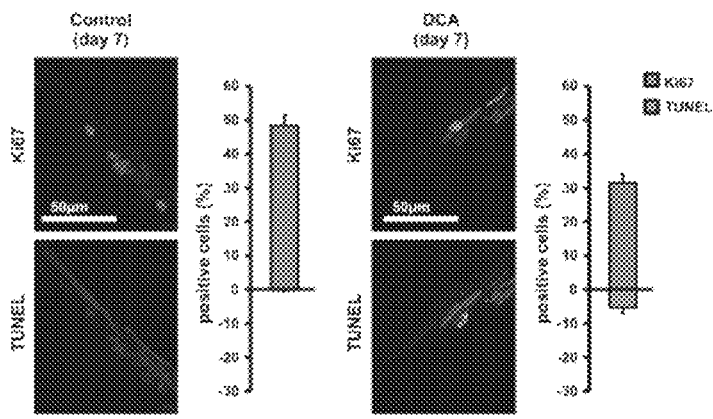
EXTENDED FIG. 6h
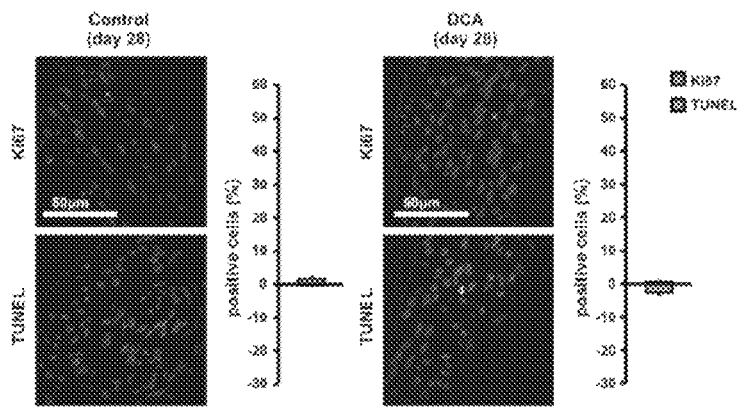
EXTENDED FIG. 6i

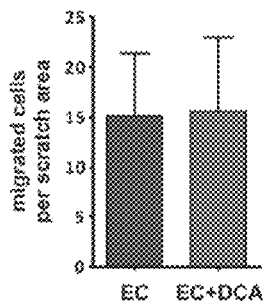
EXTENDED FIG. 7a
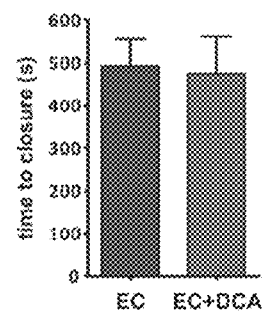
EXTENDED FIG. 7b
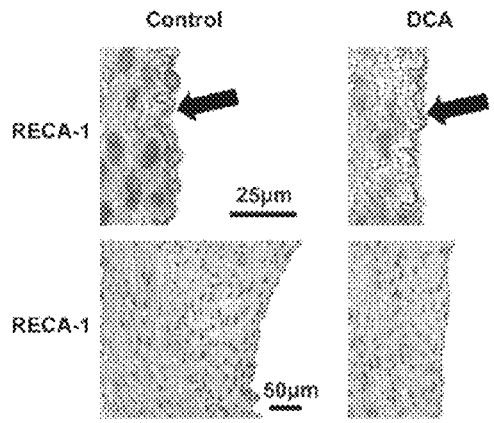
EXTENDED FIG. 7c
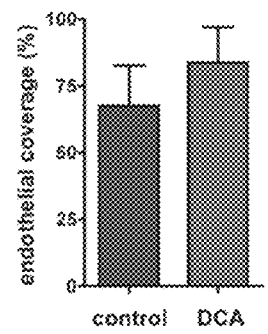
EXTENDED FIG. 7d

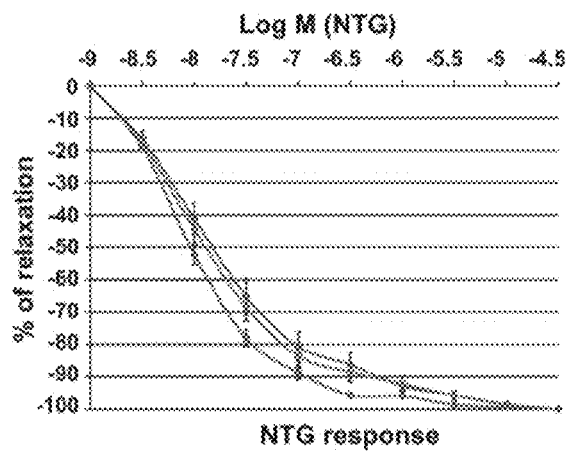
EXTENDED FIG. 7e
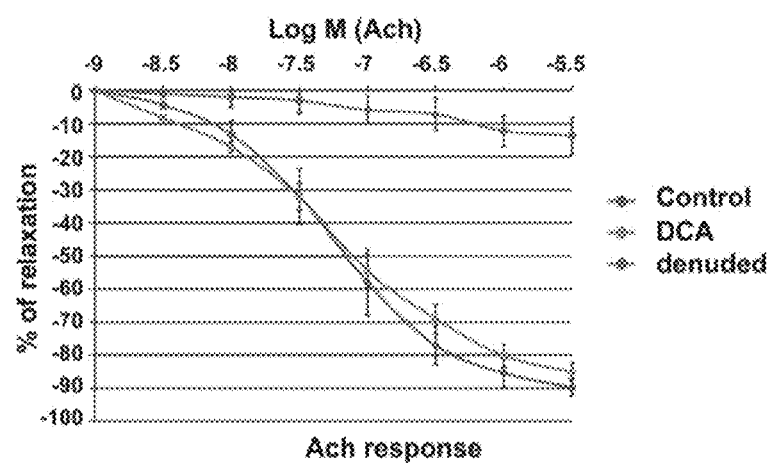
EXTENDED FIG. 7f

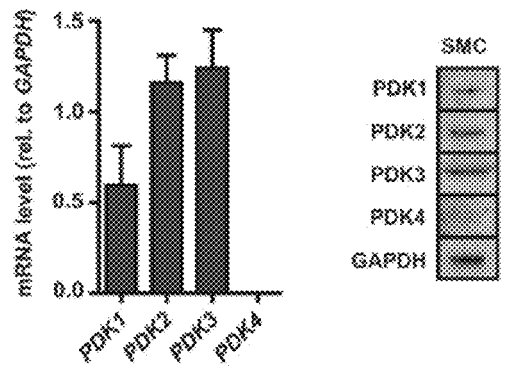
EXTENDED FIG. 8a
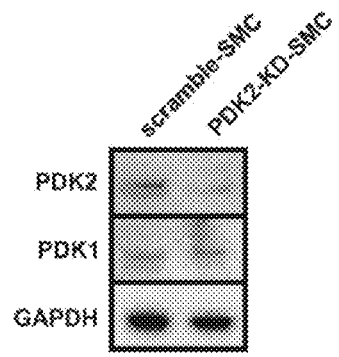
EXTENDED FIG. 8b
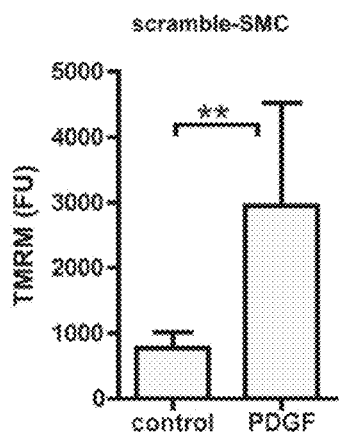
EXTENDED FIG. 8c
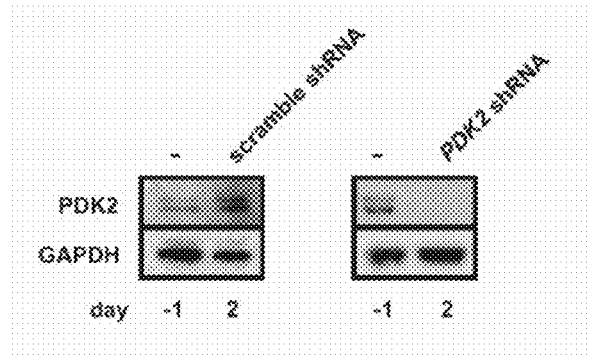
EXTENDED FIG. 8d

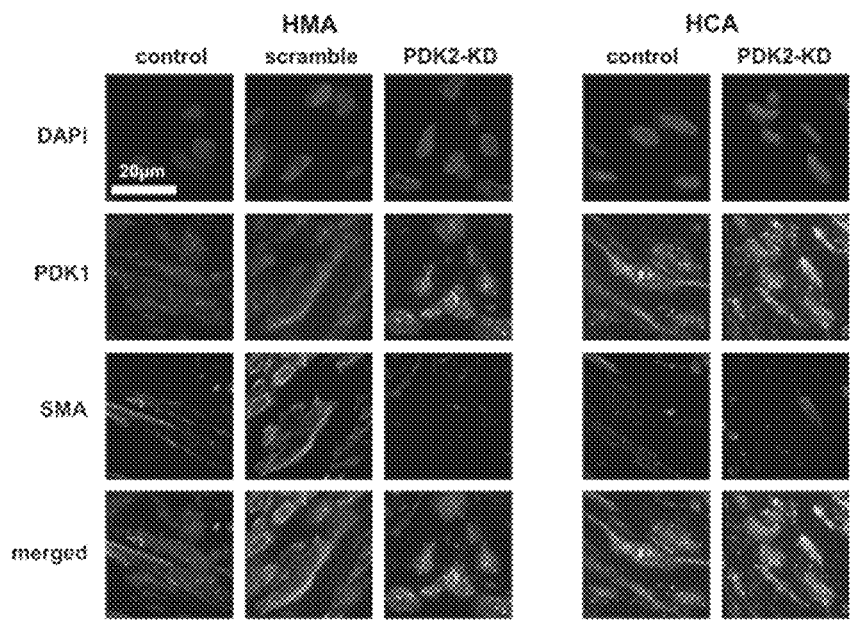
EXTENDED FIG. 8e
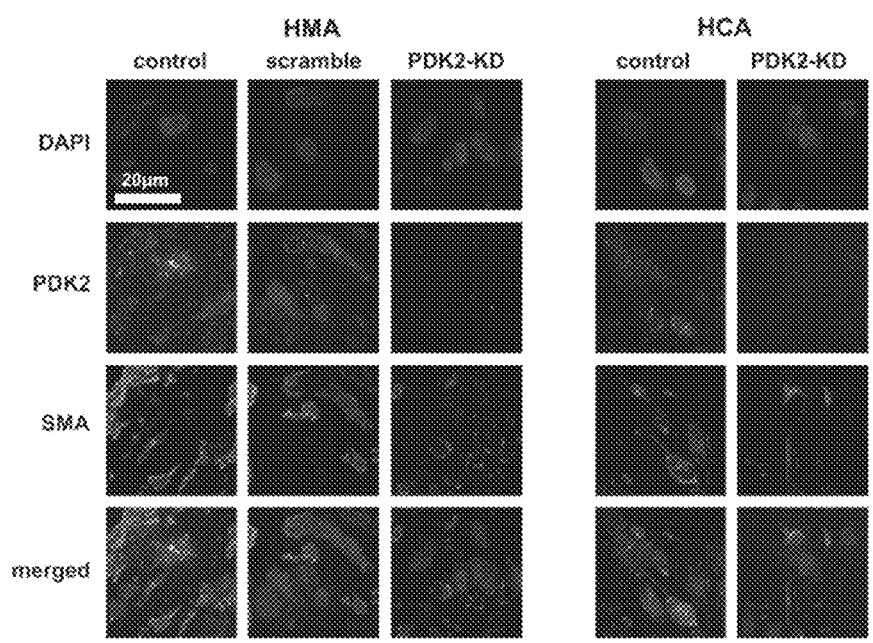
EXTENDED FIG. 8f

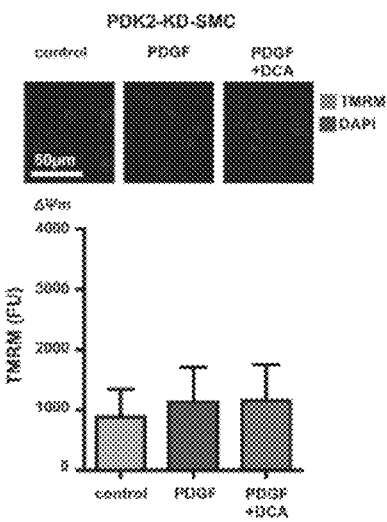
EXTENDED FIG. 9a
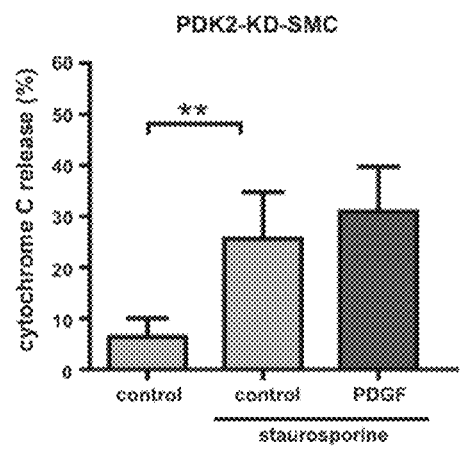
EXTENDED FIG. 9b
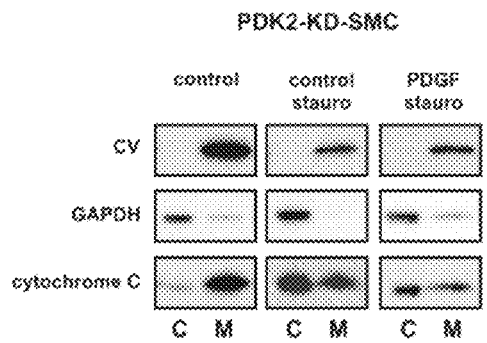
EXTENDED FIG. 9c

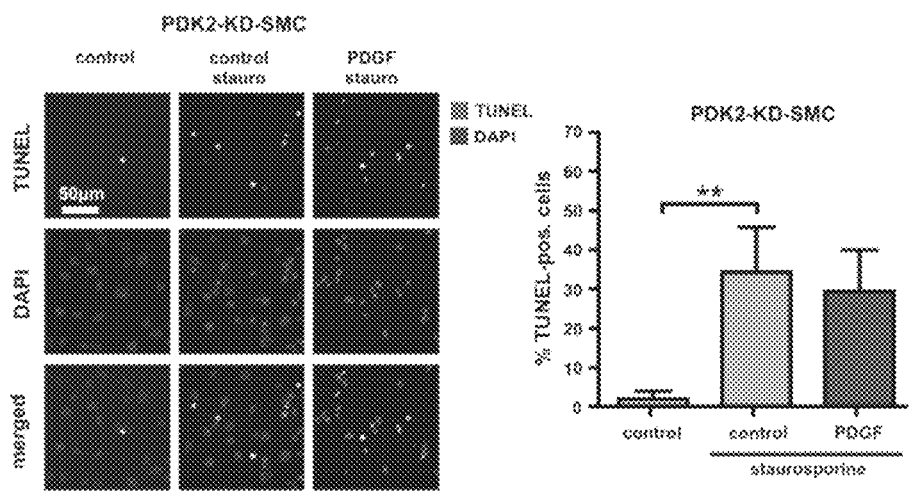
EXTENDED FIG. 9d
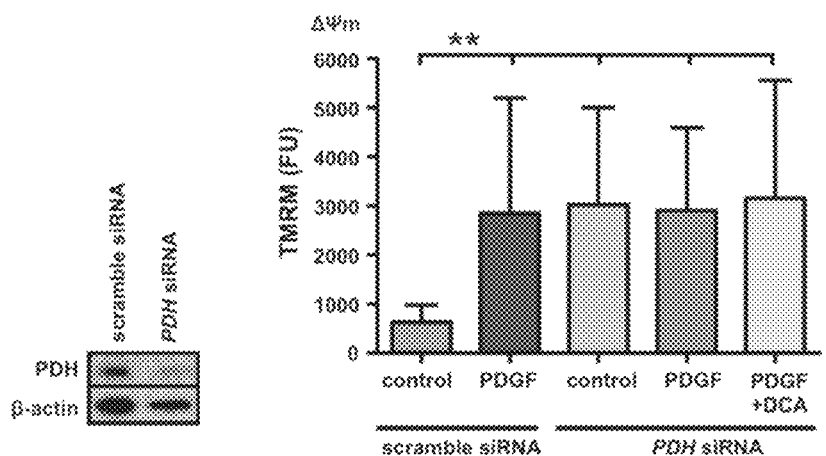
EXTENDED FIG. 9e
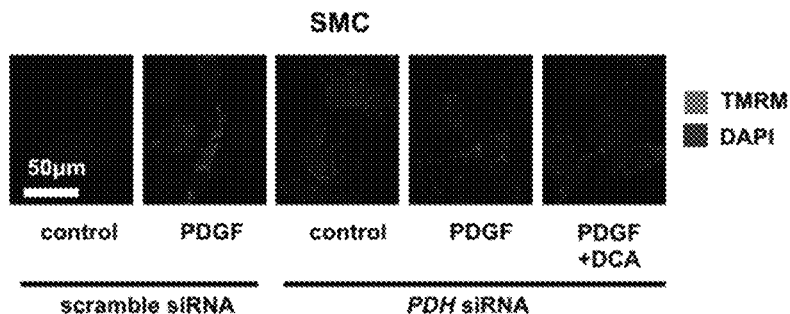
EXTENDED FIG. 9f

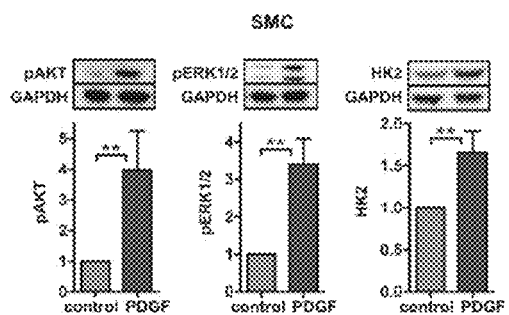
EXTENDED FIG. 10a
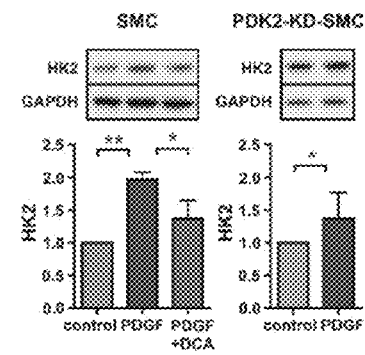
EXTENDED FIG. 10b
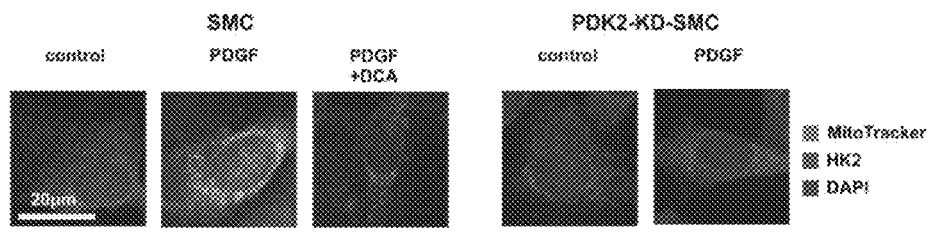
EXTENDED FIG. 10c
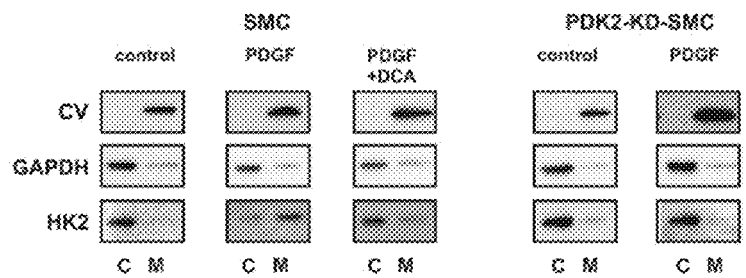
EXTENDED FIG. 10d

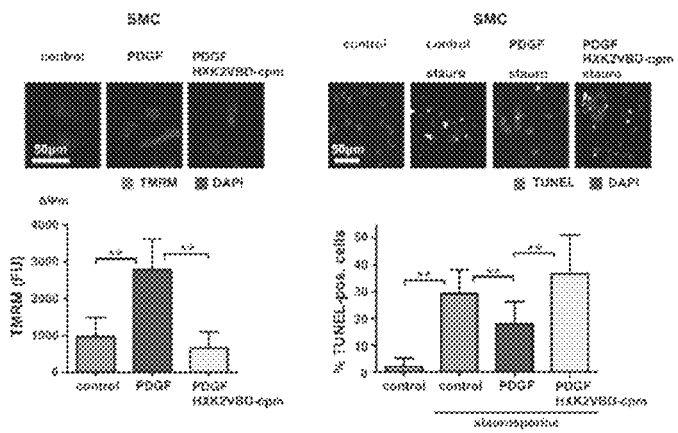
EXTENDED FIG. 10e
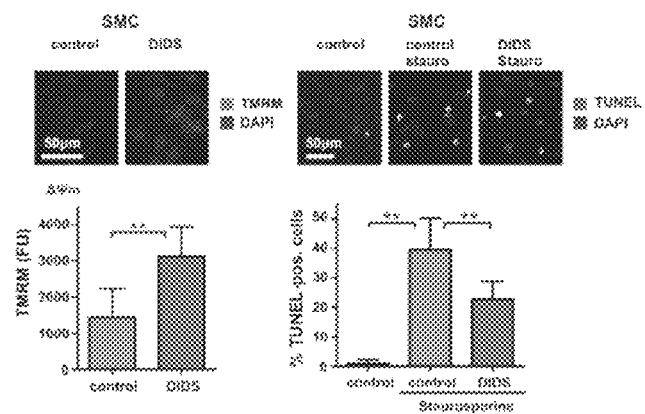
EXTENDED FIG. 10f
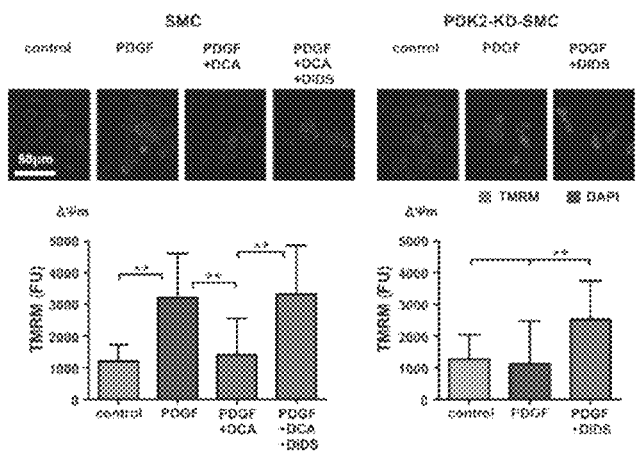
EXTENDED FIG. 10g

COMPOSITIONS AND METHODS FOR INHIBITING INTIMAL HYPERPLASIA

RELATED APPLICATION DATA

This application claims benefit of provisional application Ser. No. 62/038,206, filed Aug. 16, 2014, the entire disclosure of which is expressly incorporated by reference herein.

FIELD OF THE INVENTION

The present invention relates to compositions, kits, and methods for inhibiting, preventing and/or treating vascular diseases. For example, the compositions and methods may inhibit the development of intimal hyperplasia and/or re-stenosis, e.g. by targeting mitochondrial activity using dichloroacetate (DCA).

SUMMARY

The present invention is directed to compositions, kits, and methods for treating vascular diseases, e.g., intimal hyperplasia and/or re-stenosis within blood vessels, grafts, and other body structures, e.g., to reduce the risk of bypass graft failure.

Myointimal hyperplasia is a pathological process of the vascular system characterized by abnormal proliferation of smooth muscle cells of the vascular wall, Myointimal hyperplasia may occur in patients, for example, after vessel injury (e.g., after balloon dilatation, stent placement, and the like), or after pathological injury of the vessel (e.g., due to inflammation, toxic exposure, and the like). As described elsewhere herein, dichloroacetate ("DCA") may be useful for inhibiting, preventing, and/or otherwise treating myointimal hyperplasia.

As described elsewhere herein, a translational humanized model to study the development of intimal hyperplasia was developed. Using this model, the role of mitochondrial activity in the development of intimal hyperplasia was investigated. Aberrant vascular smooth muscle cell (SMC) proliferation is the pathophysiologic hallmark of cardiovascular diseases, the leading cause of death worldwide. Although similarities in the metabolism of rapidly dividing SMC and cancer cells have been suspected, mechanistic details remain elusive. In the studies herein, it was shown that during the early development of myointimal hyperplasia in human arteries, SMC acquire a state of mitochondrial dysfunction that shifts their glucose metabolism towards aerobic glycolysis. Pyruvate dehydrogenase kinase (PDK)2 could be identified as the key regulatory protein and its activation proved necessary for the development of myointimal hyperplasia. PDK2 is activated via PDGF-triggered pathways after vessel injury and inhibits pyruvate dehydrogenase (PDH), the enzyme that regulates the mitochondrial pyruvate influx. Both pharmacologic PDK2 blockade using dichloroacetate (DCA) and lentiviral PDK2 shRNA silencing prevented mitochondrial dysfunction and reduced myointima formation in injured human mammary or coronary arteries and rat aortas. Controlling mitochondrial-dependent SMC proliferation may be a novel strategy for the prevention of re-stenosis.

In accordance with an exemplary embodiment, a method is provided for inhibiting myointimal hyperplasia is provided that includes orally administering dichloroacetate (DCA) to a patient. In exemplary embodiments, the methods may be used to inhibit myointimal hyperplasia in blood vessels or grafts, for example, coronary bypass grafts, e.g., involving the left or right internal mammary arteries (IMAs), a vein harvested from a patient's leg, a radial artery harvested from a patient's arm, and/or other allografts/xenografts harvested from the patient or a donor body.

For example, a solution of DCA may be prepared for administration to one or more patients. For example, DCA (99% from Sigma; catalog number D54702) may be added to tap water. Optionally, one or more buffers may be added to the solution to adjust the pH of the solution, e.g., to a pH of greater than about 7.5, e.g., using sodium hydroxide (NaOH) and hydrochloric acid (HCl). Such pH levels may maintain the solution substantially stable for days.

In exemplary embodiments, the amount of DCA added to the water may be provided in a predetermined ratio, e.g., based on the mass of DCA to the mass of water and/or based on the mass of the patient. In exemplary embodiments, the amount of DCA added to the water may be at least about seventy five milligrams (75 mg) of DCA per kilogram of water, at least about one hundred milligrams (100 mg) of DCA per kilogram of water, at least about one hundred twenty five milligrams (125 mg) of DCA per kilogram of water, or between about one hundred milligrams (100 mg) of DCA per kilogram of water and two hundred milligrams (200 mg) of DCA per kilogram of water. In other embodiments, a relatively high dose may be provided, e.g., at least about five hundred milligrams (500 mg) of DCA per kilogram of water, at least about six hundred milligrams (600 mg) of DCA per kilogram of water, at least about seven hundred milligrams (700 mg) of DCA per kilogram of water, or at least about seven hundred fifty milligrams (750 mg) of DCA per kilogram of water.

In addition or alternatively, the amount of DCA solution administered may be based on the weight of the patient. For example, the patient may be administered (or instructed to self-administer) a daily dose of at least about seventy five milligrams (75 mg) per kilogram of the patient's weight, or at least about one hundred milligrams (100 mg) per kilogram of the patient's weight. For example, a sixty kilogram patient may be provided with a DCA solution having a concentration of about seven hundred fifty milligrams (750 mg) of DCA per kilogram of water and instructed to consume six liters (6 L) of the solution per day to administer about 4,500 mg of DCA (i.e., at about seventy five milligrams per kilogram).

In accordance with another embodiment, a kit is provided for inhibiting myointimal hyperplasia that includes a container having a predefined interior volume, and a predetermined mass of DCA within the container such that, when the container is filled to the predefined interior volume with water, the concentration of the DCA within the resulting solution has a desired concentration of DCA for oral administration. In exemplary embodiments, the ratio of the interior volume and mass of DCA may be at least about five hundred milligrams (500 mg) of DCA per kilogram of water, at least about six hundred milligrams (600 mg) of DCA per kilogram of water, at least about seven hundred milligrams (700 mg) of DCA per kilogram of water, or at least about seven hundred fifty milligrams (750 mg) of DCA per kilogram of water. Optionally, the container may also include a predetermined amount of buffer, e.g., a predetermined amount of sodium hydroxide (NaOH) and hydrochloric acid (HCl), such that the resulting solution has a pH of at least 7.5.

Other aspects and features of the present invention will become apparent from consideration of the following description taken in conjunction with the accompanying drawings.

BRIEF DESCRIPTION OF THE DRAWINGS

The invention is best understood from the following detailed description when read in conjunction with the accompanying drawings. It will be appreciated that the exemplary apparatus shown in the drawings are not necessarily drawn to scale, with emphasis instead being placed on illustrating the various aspects and features of the illustrated embodiments.

FIGS. 1a-1f show the Chronology and growth dynamics of myointima formation in the humanized hMA model. FIG. 1a shows the Development of myointimal hyperplasia. FIG. 1b shows Non-calcified lesions in naturally diseased human coronary artery. FIG. 1c shows Luminal obliteration over time. FIGS. 1d-1e show the timeline of proliferative and apoptotic activity within the myointima was monitored by immunofluorescence and quantified. FIG. 1f shows ΔΨm in hMA myointima.

FIGS. 2a-2f show that DCA alleviates myointima formation in vivo. FIG. 2a shows that, after 28 days, luminal obliteration was significantly less in the DCA group of the hMA model. FIG. 2b shows myointimal growth dynamics in the hMA DCA group. FIG. 2c shows that, in hMA DCA21 vessels, ΔΨm was significantly lower than in control arteries. FIG. 2d shows that DCA reduced luminal obliteration in the hCor model. FIGS. 2e-2f show that DCA effectively alleviated myointima formation in balloon-injured rat aortas.

FIGS. 3a-3d show that PDK2-KD alleviates myointima formation in vivo. FIG. 3a shows that PDK2-KD hMA showed elevated apoptosis rates during the early time points of increased proliferative activity resulting in low myointimal net proliferation. FIG. 3b shows that ΔΨm in PDK2-KD21 was similarly low as in DCA21 hMA vessels. FIG. 3c shows that luminal obliteration was significantly reduced in PDK2-KD28 hMA compared to scrambled shRNA controls. FIG. 3d shows that luminal obliteration was low in PDK2-KD28 hCor vessels.

FIG. 4a shows that, after 28 days, the coronary arteries of untreated and DCA-treated Yorkshire swine were retrieved. FIG. 4b shows that the patent lumen inside the external elastic lamina was significantly larger in the DCA group. Thus, DCA significantly alleviated myointima formation. FIGS. 4c-d show that, in the region of a ruptured internal elastic lamina, the proliferation area (c) and the maximal proliferation thickness (d) were significantly smaller with DCA.

Extended Data FIGS. 1g-1o show Myointima formation in balloon-injured rat aortas. Extended FIGS. 1g-1h show that, 48 h after mechanical injury, trichrome (a) and immunofluorescence for SMC-markers (b) identified abundant SMCs in the aortic media. Extended FIG. 1i shows that the infiltrate at 48 h was composed of CD68+ macrophages, some MPO+ neutrophils, and no CD3+ lymphocytes. Extended FIG. 1i shows that Akt- and Erk1/2 phosphorylation was markedly increased as early as 30 min. after injury. Extended FIG. 1k shows that media cells of injured aortas showed ΔΨm hyperpolarization after 48 h. Extended FIGS. 1l-1m show that a myointima developed over 28 days in injured rat aortas and caused luminal obliteration. Extended FIG. shows that many infiltrating macrophages and very few neutrophils were observed in the myointima at 7 days. Extended FIG. 1o, shows that tissue IFN-γ, MCP-1, MIP-3α, and IL-1β levels were markedly increased at 7 days and were diminished after 28 days.

Extended Data FIGS. 2g-2i show Characterization of the hMA model. Extended FIGS. 2g-2h show that sections were co-stained for the SMC markers smoothelin, SM22, and calponin (a) or SMA, smooth muscle myosin (SM) heavy chain, and myocardin (b). Extended FIG. 2i shows that the human origin of myointimal cells in 21-day control hMAs was confirmed.

Extended Data FIGS. 3e-3k show The central role for PDGF in advancing myointima formation. Extended FIG. 3e shows that, after 28 days, non-denuded hMAs in RNU rats showed only minor myointimal lesions. Extended FIG. 3f shows that, to evaluate a possible rejection process in the xenogeneic hMA setting, host immune activation and graft infiltration were assessed. Extended FIG. 3g shows that immunohistochemistry identified myointimal macrophages and neutrophils in hMA control specimens and reduced leukocyte infiltration in control specimens, and lymphocytes were not observed. Extended FIG. 3h shows that hMA tissue levels of the inflammatory cytokines IFN-γ, MCP-1, MIP-3α, and IL-1β were elevated during the first 14 days. Extended FIG. 3i shows that, in hMA21 vessels, spatial differences of SMC ΔΨm with higher TMRM fluorescence in the luminal areas compared to the areas adjacent to the media were observed. Extended FIG. 3j shows that tissue PDGF was increased in hMA after injury and peaked after 14 days. Extended FIG. 3k shows that, compared to untreated control 28 vessels in the rat aortic balloon injury model, imatinib (PDGF-R blocker)-treated vessels showed only minor lesions.

Extended Data FIGS. 4e-4h show SMC characterization and response to PDGF. Extended FIGS. 4e-4f show that cells isolated from fresh hMA were positive for SMA, myocardin, smoothelin, calponin, and SM22α (SM22) as detected by FACS and immunofluorescence. Extended FIG. 4g shows that ΔΨm hyperpolarization, a phenomenon observed at times of maximized net proliferative activity in hMA, could be linked to PDGF. Extended FIG. 4h shows a significant down-regulation of c-kit, SMA, and SM22 mRNA vs. GAPDH mRNA after incubation with PDGF, all maturity markers for contractile SMCs.

Extended Data FIGS. 5a-5e show DCA reduces ΔΨm hyperpolarization and facilitates apoptosis in SMCs. Extended FIG. 5a shows that, to assess the kinetic of DCA action in vitro, SMCs were pre-incubated with DCA for different time periods and then stimulated with PDGF for 48 h. Extended FIG. 5b shows that atherosclerotic plaques from heavily calcified and atherosclerotic human coronary arteries were scraped off the media and cultured in SMC medium. Extended FIGS. 5c-5e show that apoptosis induction with staurosporine significantly increased the number of control SMCs that showed cytochrome C leakage, as identified by diffuse cytochrome C staining throughout the cell.

Extended Data FIGS. 6a-6i show DCA lowers medial and myointimal ΔΨm and facilitates apoptosis in balloon-injured rat aortas. Extended FIGS. 6a-6b show that trichrome (a) and immunofluorescence (b) confirmed abundant SMCs in the aortic media of DCA-treated animals 48 h after injury. Extended FIG. 6c shows that, similar to control vessels, the infiltrate mainly contained macrophages and neutrophils, but no CD3+ lymphocytes. Extended FIG. 6d shows that DCA reduced ΔΨm of medial cells. Extended FIG. 6e shows that macrophages were the main inflammatory cell population in the developing myointima of immunocompetent DCA animals at 7 days. Extended FIGS. 6f-6g shows that DCA effectively lowered the elevated ΔΨm of myointimal cells on day 7, but had little effect on the already reduced ΔΨm at 28 days. Extended FIGS. 6h-6i show that the percentages of proliferating and apoptotic cells in the myointima were calculated.

Extended Data FIGS. 7a-7f show DCA does not impair EC migration or vessel re-endothelialization. Extended FIGS. 7a-7b show that a scratch was made across a confluent human EC monolayer. Extended FIGS. 7c-7d show that, to evaluate vessel reendothelialization, rat aortas underwent mechanical endothelial denudation by balloon injury. Extended FIGS. 7e-7f show that endothelial function in both 28-day groups was further assessed in relaxation studies and compared to denuded aortas three days after balloon injury.

Extended Data FIGS. 8a-8f show PDK2 knock-down in SMCs, hMA, and hCor. Extended FIG. 8a shows that PDK1-4 mRNA expression was assessed in control SMCs and normalized to. Extended FIG. 8b shows that, to confirm in vitro PDK2 knock-down, PDK1 and PDK2 expressions were assessed in immunoblots. Extended FIG. 8c shows that, to exclude that lentiviral shRNA transduction changed the ΔΨm response to PDGF, SMCscramble were stimulated with. Extended FIG. 8d shows that fresh hMA vessels underwent balloon injury, were divided, and one half was sampled (day −1). Extended FIGS. 8e-8f show that, after 28 days, hMA and hCor samples were stained for DAPI, PDK1, PDK2, and SMA. PDK1 was similarly detectable in all control 28, scramble 28, and PDK2-KD28 sections.

Extended Data FIGS. 9a-9f show PDK2-KD mimics the DCA-effect on SMC ΔΨm and apoptosis. Extended FIG. 9a shows that PDK2-KD-SMCs were pre-incubated with DCA and/or stimulated with PDGF. Extended FIGS. 9b-9c show that apoptosis was induced with staurosporine. Extended FIG. 9e shows that, to establish a link between PDH and ΔΨm, PDH was knocked down. Extended FIG. 9f shows that ΔΨm was significantly increased in PDH siRNA-transfected SMCs and PDGF and DCA did no longer affect ΔΨm.

Extended Data FIGS. 10a-10g show VDAC controls ΔΨm and apoptosis. Extended FIG. 10a shows that PDGF stimulation of SMCs significantly increased phosphorylated Akt and Erk1/2 and increased the expression of HK2. Extended FIG. 10b shows that immunoblots revealed PDGF-induced up-regulation of HK2 expression in SMCs. Extended FIG. 10c shows that confocal images with mitochondrial, HK2, and nuclear staining were captured. Extended FIG. 10d shows that cytoplasmatic (C) and mitochondrial fractions (M) were isolated for immunoblotting. Extended FIG. 10e shows that, in the presence of HXK2VBD-cpm, PDGF failed to induce both ΔΨm hyperpolarization and apoptosis resistance. Extended FIG. 10f shows that VDAC inhibition by DIDS caused ΔΨm hyperpolarization and rendered SMCs resistant to staurosporine-induced apoptosis. Extended FIG. 10g shows that the depolarizing effect of DCA on PDGF-treated SMCs was counteracted by DIDS.

DETAILED DESCRIPTION OF THE EXEMPLARY EMBODIMENTS

Despite the introduction of antiproliferative drug-eluting stents, coronary heart disease remains the leading cause of death in the United States. In-stent re-stenosis and bypass graft failure are characterized by excessive smooth muscle cell (SMC) proliferation and concomitant myointima formation with luminal obliteration. During the development of myointimal hyperplasia in human arteries, SMCs show hyperpolarization of their mitochondrial membrane potential (ΔΨm) and acquire a temporary state with high proliferative rate and resistance to apoptosis. Pyruvate dehydrogenase kinase (PDK)2 is a key regulatory protein, and its activation proved necessary for relevant myointima formation. Pharmacologic PDK2 blockade with dichloroacetate (DCA) or lentiviral PDK2 knock-down prevented ΔΨm hyperpolarization, facilitated apoptosis, and reduced myointima formation in injured human mammary and coronary arteries, rat aortas, rabbit iliac arteries, and swine coronary arteries. In contrast to several commonly used antiproliferative drugs, DCA did not prevent vessel re-endothelialization. Targeting myointimal ΔΨm and alleviating apoptosis resistance is a novel, not yet utilized strategy for the prevention of proliferative vascular diseases.

Figure 1B:

In the studies described elsewhere herein, balloon-injury of Lewis rat aortas triggered an inflammatory response and caused leukocyte infiltration in the SMC-rich media after 48 h, consisting mainly of CD68+ macrophages and some myeloperoxidase (MPO)+ neutrophils; CD3+ lymphocytes were not observed (Extended Data FIGS. 1g-i). Compared to healthy, non-injured aortas, we observed increased phosphorylation of Akt and Erk1/2 and ΔΨm hyperpolarization in media cells of injured vessels (Extended Data FIGS. 1j-k). A myointima subsequently developed luminal to the internal elastic lamina, which caused progressive luminal obliteration over 28 days (Extended Data FIGS. 1l-m). This process was accompanied by leukocyte infiltration and inflammatory cytokine release, which was strong after seven (7) days and markedly reduced at twenty eight (28) days (Extended Data FIGS. 1n-1o). A humanized model was subsequently developed to longitudinally study myointima formation in human arteries.

Figure 1C:
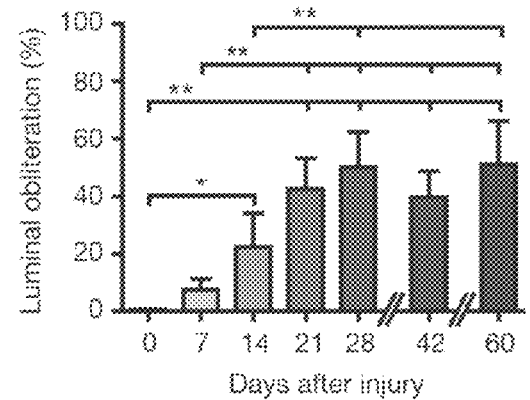

Balloon-injured human internal mammary arteries (hMA) were implanted into the abdominal aortic position of T cell-deficient RNU-rats. Myointimal hyperplasia rapidly developed over four weeks (FIG. 1a) causing progressive luminal obliteration (FIG. 1c). By histopathology (FIG. 1b) and confocal immunofluorescence (Extended Data FIGS. 2g-h), the myointima in the hMA model after twenty eight (28) days or later closely resembled lesions of diseased human coronary arteries retrieved from autopsy samples. Using HLA I- and rat MHC I-antibodies, the human origin of the SMCs within the myointima was confirmed (Extended Data FIG. 2i). Only the mechanical vessel injury was causally related to myointima formation and no relevant xenoantigen-triggered immune activation was observed (Extended Data FIGS. 3e-f). Similar to the immunocompetent Lewis rat aortic injury model, we observed accumulation of CD68+ macrophages and MPO+ neutrophils in hMA vessels after seven days, which was markedly attenuated by day 28 (Extended Data FIG. 3g). Immune cell infiltration was again accompanied by the elevation of inflammatory cytokines (Extended Data FIG. 3h).

Figure 1D:
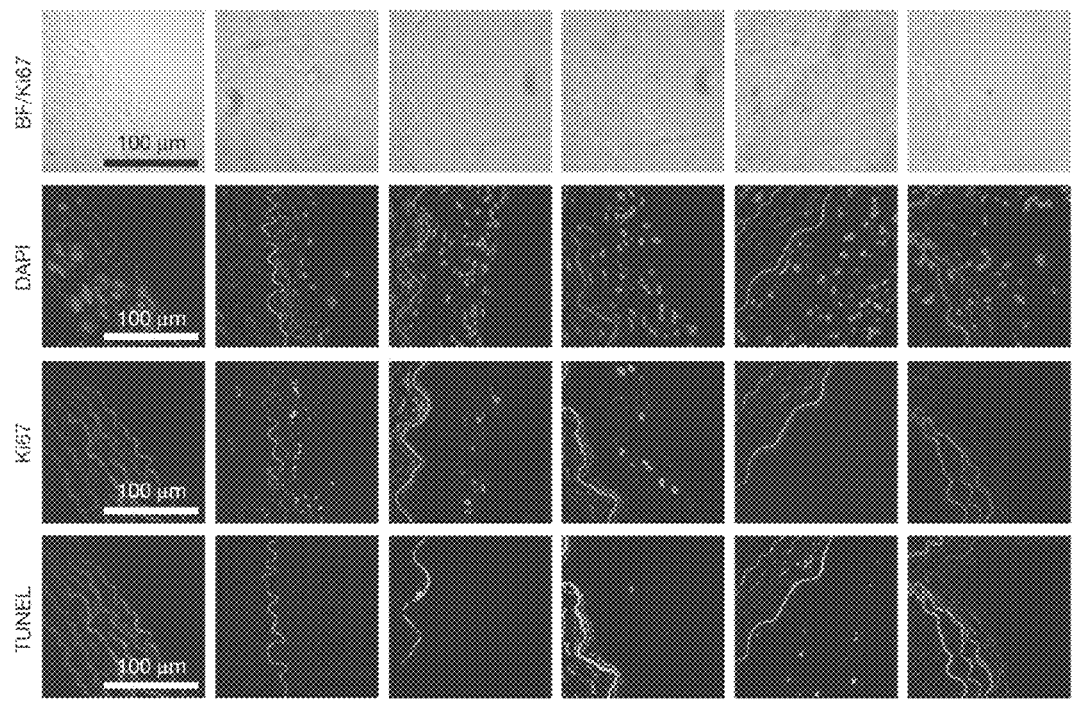
Figure 1E:
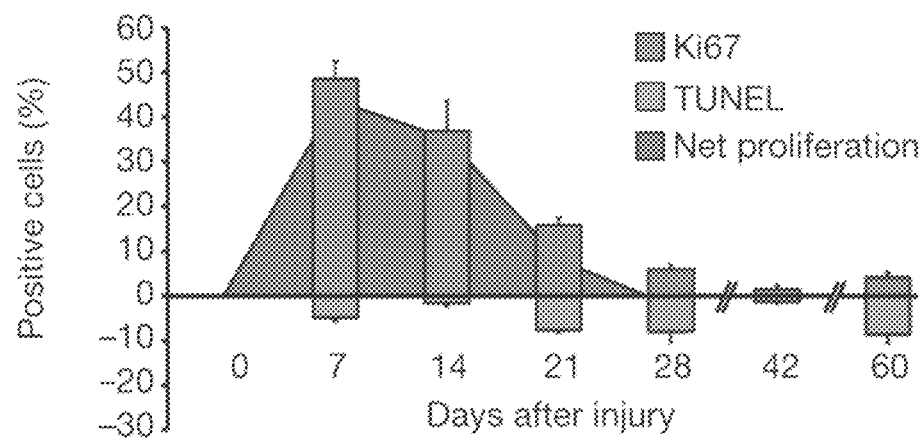
Figure 1F:
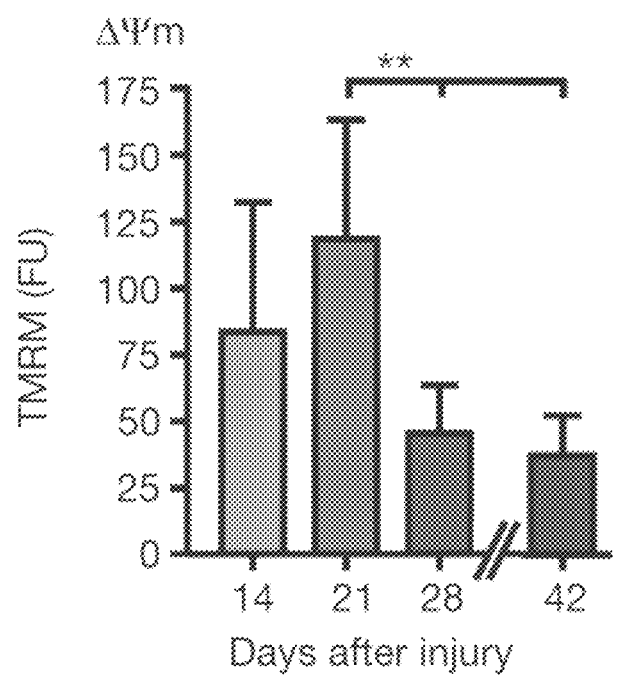
Figure 4A:
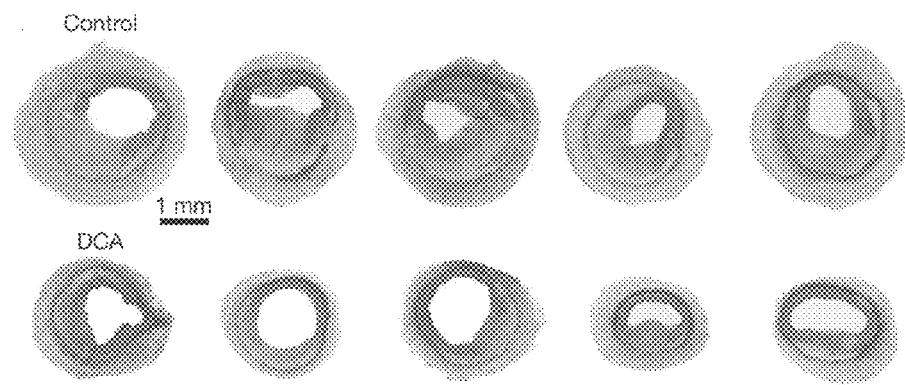
FIGS. 4a-4d show that DCA effectively reduces balloon injury-induced myointima formation in swine coronary arteries in vivo.
Figure 4B:
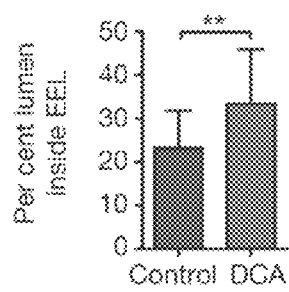
Figure 4C:
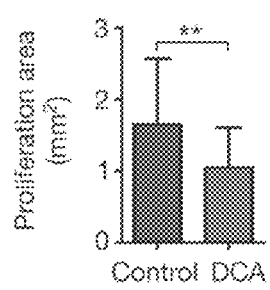
Figure 4D:
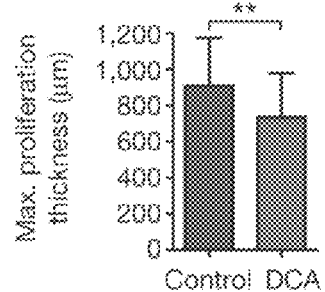

Analysis of cell growth dynamics in hMA showed a transient but strong increase in proliferative activity within the myointima between seven and twenty one (7-21) days after injury, accompanied by a persistently low rate of apoptosis (FIGS. 1d-e). Proliferation and apoptosis leveled off after twenty eight (28) days when there was also no further progression of myointimal disease (FIGS. 1c, 1e). Only during the time period of highly positive net proliferation did myointimal cells demonstrate ΔΨm hyperpolarization (FIG. 10. Within the myointima, cells in the luminal region showed higher proliferative activities and higher ΔΨm than cells closer to the media (Extended Data FIG. 3i). PDGF was suspected to be the major driving factor promoting myointimal hyperplasia as it was temporarily increased in injured hMA vessels and PDGF receptor blockade prevented the development of relevant disease (Extended Data FIGS. 3k-3k). Human vascular SMCs were isolated from fresh hMA and characterized (Extended Data FIGS. 4e-4f). PDGF was then shown to induce $\Delta\Psi m$ hyperpolarization in cultured SMCs (Extended Data FIG. 4g), similar to the $\Delta\Psi m$ hyperpolarization previous observed in injured hMAs (FIG. 1f). Thus, mitochondrial $\Delta\Psi m$ hyperpolarization in myointimal SMCs and cultured SMCs coincided with the availability of PDGF. PDGF also caused a phenotype switch in SMCs from a contractile to a dedifferentiated state (Extended Data FIG. 4h).

Mitochondria have been shown to regulate apoptosis via their mitochondrial apoptotic pathway. This involves mitochondrial permeability transition and the release of toxic components such as cytochrome C and caspases. In this context, $\Delta\Psi m$ plays an important role in the control of the mitochondrial permeability transition pore, as $\Delta\Psi m$ hyperpolarization has been suspected to impede pore opening. DCA, a rapid-acting small molecule targeting mitochondrial PDKs, has previously been demonstrated to reduce $\Delta\Psi m$ in A549 cells. Because elevated $\Delta\Psi m$ and suppressed apoptosis have been observed after injury in our hMA model, we hypothesized DCA would prevent post-injury $\Delta\Psi m$ hyperpolarization, facilitate apoptosis, and reduce myointimal growth.

DCA effectively prevented $\Delta\Psi m$ hyperpolarization in PDGF-treated SMCs isolated from either healthy or atherosclerotic vessels (Extended Data FIGS. 5a-5b). Previously, mitochondrial cytochrome C release and apoptosis induction were shown to be suppressed by hyperpolarized $\Delta\Psi m$. Consistent with this observation, PDGF reduced staurosporine-induced mitochondrial cytochrome C leakage (Extended Data FIGS. 5c-5d) and rendered SMCs resistant to apoptosis (Extended Data FIG. 5e). DCA both increased cytochrome C release and restored the ability to enter apoptosis (Extended Data FIGS. 5c-5e).

In vivo, oral DCA did not affect leukocyte infiltration in the media of balloon-injured aortas in immunocompetent Lewis rats, but effectively lowered $\Delta\Psi m$ in the media at 48 h (Extended Data FIGS. 6a-d). The accumulation of CD68+ macrophages and MPO+ neutrophils in the developing myointima was also not affected by DCA (Extended Data FIG. 6e). However, at seven days, DCA markedly reduced myointimal $\Delta\Psi m$ and permitted apoptosis (Extended Data FIGS. 6f, 6h). At twenty eight (28) days, $\Delta\Psi m$ in the developed control myointima had already lowered and DCA showed little effect (Extended Data FIG. 6g). Also, proliferation and apoptosis were low at that time point (Extended Data FIG. 6i).

Figure 2D:
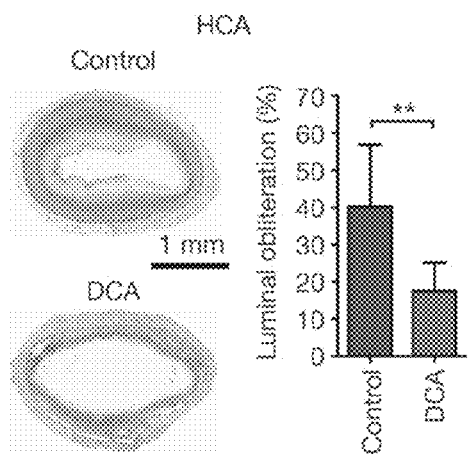
Figure 2E:
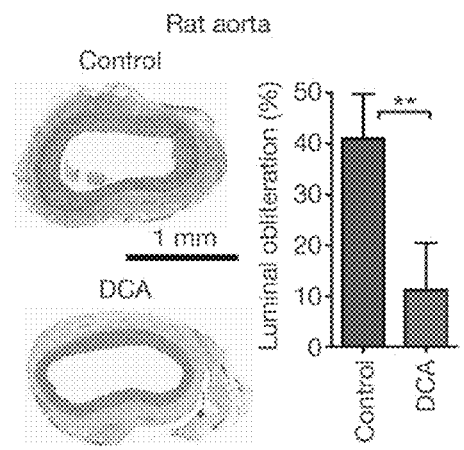
Figure 2F:
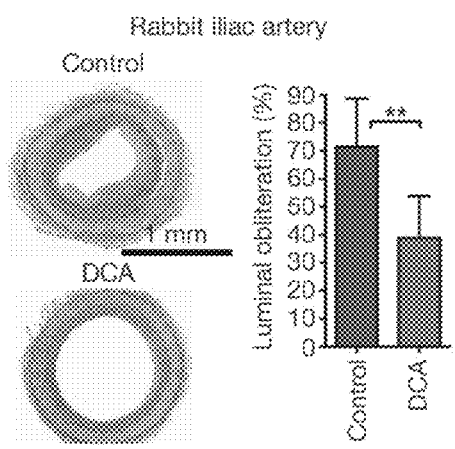

The potential vasculoprotective effect of DCA was then tested in the hMA and hCor (human coronary artery) models (FIGS. 2a-2d). For the latter, human coronary arteries with minor pre-existing disease, which underwent the same balloon injury and implantation procedure as described for hMA, were used to better reflect the coronary pathophysiology. Oral DCA administration strongly reduced the development of myointima and luminal narrowing in both hMA (FIG. 2a) and hCor (FIG. 2d). Similar to untreated hMA controls, the proliferative response to injury in DCA-treated vessels was strongest within the first fourteen (14) days and weakened thereafter (FIG. 2b). The apoptotic activity, however, was also enhanced and mirrored the proliferative activity at each time point, resulting in a much lower net proliferation. In accordance with the in vitro data, we observed significantly lower $\Delta\Psi m$ in the 21-day hMA specimens of the DCA group (FIG. 2c). To exclude that ischemia-reperfusion injury or xenogeneic immune interactions may have affected our results, DCA was further tested in the rat aortic (FIG. 2e) and the rabbit iliac artery balloon injury model (FIG. 2f). Again, myointima formation after twenty eight (28) days was remarkably reduced by DCA in both models. Interestingly, DCA neither demonstrated antimigratory effects on endothelial cells in vitro, nor inhibited vessel re-endothelialization in vivo (Extended Data FIG. 7).

PDKs are the only known targets of DCA and PDKs exclusively phosphorylate and thus inactivate pyruvate dehydrogenase (PDH). It was thus suspected that PDK knock-down would generate similar biological effects as PDK inhibition by DCA. Although SMCs express PDK1-3 (Extended Data FIG. 8a), PDK2 has the highest affinity to DCA10 and likely mediates the vast majority of the DCA effect. Therefore, PDK2-knock-down (KD)-SMCs were generated using PDK2 lenti-shRNA (Extended Data FIG. 8b-8c) to verify the mechanistic involvement of PDK2 in the DCA effect. Indeed PDK2-KD-SMCs maintained steadily low $\Delta\Psi m$ (Extended Data FIG. 9a) under control conditions and with PDGF stimulation. Also, PDK2-KD-SMCs maintained increased cytochrome C release and elevated apoptotic rates even during PDGF incubation (Extended Data FIGS. 9b-9d). In addition, DCA lost its ability to affect $\Delta\Psi m$ in PDK2-KD-SMCs (Extended Data FIG. 9a). As expected, when PDH (the primary inhibitory target of PDK2) was knocked down (Extended Data FIG. 9e) instead of PDK2, the opposite effect was observed: $\Delta\Psi m$ was permanently elevated, even under control conditions (Extended Data FIG. 9f). DCA again lost its ability to depolarize $\Delta\Psi m$, indicating that the DCA effect on $\Delta\Psi m$ depended on both PDK2 and PDH.

To assess whether arteries with ex vivo PDK2 knockdown would develop similarly reduced myointima as arteries under DCA treatment, PDK2-KD was induced in hMA and hCor before implantation (Extended Data FIG. 8d-8f). Comparable to the DCA group, PDK2-KD hMA showed low net proliferation throughout the 28-day study period (FIG. 3a). $\Delta\Psi m$ hyperpolarization was also effectively prevented and the low $\Delta\Psi m$ of PDK2-KD21 hMA (FIG. 3b) closely resembled the $\Delta\Psi m$ values of DCA21 hMA (FIG. 2c). Reduced luminal obliteration was observed in both PDK2-KD28 hMA (FIG. 3c) and hCor (FIG. 3d).

DCA was ultimately evaluated in a translationally relevant swine model of coronary artery re-stenosis. Yorkshire swine underwent standardized coronary artery balloon injury under fluoroscopic guidance. After twenty eight (28) days, DCA-treated animals showed significantly reduced luminal obliteration, proliferation area, and max. proliferation thickness (FIGS. 4a-4d). In summary, DCA reduced myointima formation in five different pre-clinical in vivo models.

Upon PDGF stimulation of cultured SMCs, we observed an activation of the downstream PI3K and MEK pathways with Akt- and Erk1/2-phosphorylation, hexokinase2 (HK2) upregulation, and increased HK2-mitochondrial association (Extended Data FIGS. 10a-10d). HK2 has previously been shown to have a binding site close to VDAC, the most abundant protein of the outer mitochondrial membrane, and HK2 binding was reported to reduce channel conductance. In line with this previous work, we show that HK2-mitochondrial association coincided with $\Delta\Psi m$ hyperpolarization and apoptosis resistance in our study. Furthermore, displacement of HK2 from its mitochondrial VDAC binding site both reduced $\Delta\Psi m$ and restored the susceptibility to apoptosis (Extended Data FIG. 10e). VDAC closure using the inhibitor DIDS also increased SMC $\Delta\Psi m$ and reduced apoptosis (Extended Data FIG. 10f), further supporting the direct mechanistic involvement of VDAC in the regulation of both $\Delta\Psi m$ and apoptosis.

DCA and PDK2-KD diminished HK2 elevation (Extended Data FIG. 10b) and HK2-mitochondrial association (Extended Data FIGS. 10c-10d), and maintained low $\Delta\Psi m$ despite PDGF (Extended Data FIG. 10g). Notably, it was confirmed that the depolarizing effects of DCA and PDK2-KD on $\Delta\Psi m$ were ultimately mediated through VDAC, because inhibition of VDAC opening by DIDS was found to neutralize these effects (Extended Data FIG. 10g). The mechanistic link between PDK2 inhibition and the decrease in HK2-VDAC binding and reversal of $\Delta\Psi m$ hyperpolarization, however, remains elusive.

In healthy vessels, proliferation and apoptosis are very low and balanced. Vessel injury disrupts this homeostasis and triggers an inflammatory state, which induces temporary $\Delta\Psi m$ hyperpolarization in SMCs and drives myointima formation. As shown herein, PDK repression counteracts temporarily acquired apoptosis resistance and may be a well-tolerated strategy for the prevention of re-stenosis without interfering with re-endothelialization.

Thus, the objective of the studies described herein and Ser. No. 62/038,206 was to evaluate if the mitochondrial modulator dichloroacetate (DCA) can be used to inhibit intimal hyperplasia, which occurs in different diseases, such as after vessel injury and stent placement as well as atherosclerosis. All of the references identified in Appendix A of Ser. No. 62/038,206 are expressly incorporated by reference herein.

For example, abdominal aortic denudation in Lewis rats was performed to induce neointimal proliferation. In the treatment groups, the mitochondrial modulator dichloroacetate (DCA) was given at different time points via drinking water (0.75 g/L). The development of intimal hyperplasia was analyzed by histopathology. Confocal immunofluorescence microscopy and 3-dimensional reconstruction was performed to identify cell proliferation (Ki67) and apoptosis (TUNEL). ApoE−/− mice were fed an atherogenic western diet for 5 months and animals were treated with either DCA or left untreated (n=10/group). Atherosclerotic lesions were identified using Sudan III staining followed by computer morphometry.

Developed ideal luminal obliteration in untreated animals on day fourteen (14) and twenty eight (28) was 12.7±12.9% and 24.2±3.5%, respectively. DCA treatment for twenty eight (28) days significantly reduced intimal hyperplasia (7.9±6.3%, p=0.006 vs. untreated 28-day control). Delayed DCA treatment starting on day fourteen (14) resulted in significantly reduced neointimal formation (3.5±2.9%, p=0.001 vs. untreated 28-day control). Interestingly, early and delayed treatment of DCA induced apoptosis resulting in shrinking hyperplasia area (p=0.014 and p=0.005 vs. untreated control). TUNEL positive apoptotic cells within the intimal hyperplasia were significantly increased in the DCA treated animals after 28 d (p=0.006 vs. untreated animals). No significant reduction in atherosclerotic plaque formation was observed.

In accordance with an exemplary embodiment, DCA is used via oral administration to inhibit, prevent, or otherwise treat myointimal hyperplasia, e.g., since DCA didn't show any side-effects or off-target effects in our various in vivo models.

Initially, a solution of DCA is prepared for administration to one or more patients. For example, DCA (99% from Sigma; catalog number D54702) may be added to tap water. Optionally, one or more buffers may be added to the solution to adjust the pH of the solution, e.g., to a pH of greater than about 7.5, e.g., using sodium hydroxide (NaOH) and hydrochloric acid (HCl). Such pH levels may maintain the solution substantially stable for days.

In exemplary embodiments, the amount of DCA added to the water may be provided in a predetermined ratio, e.g., based on the mass of DCA to the mass of water. In exemplary embodiments, the amount of DCA added to the water may be at least about seventy five milligrams (75 mg) of DCA per kilogram of water, at least about one hundred milligrams (100 mg) of DCA per kilogram of water, or between about one hundred milligrams (100 mg) of DCA per kilogram of water and two hundred milligrams (200 mg) of DCA per kilogram of water.

Individual doses may be provided to a patient, e.g., such that the patient drinks one dose at set intervals, e.g., multiple times a day, e.g., one to three (1-3) times per day. Exemplary individual doses may be between about half to one liter (0.5-1.0 L) each. Alternatively, a daily dose may be provided to a patient, e.g., about one to two liters (1.0-2.0 L) of the solution, such that the patient drinks the daily dose over the course of a single day, e.g., at set intervals or simply intermittently such that the dose is consumed over the course of the day.

For example, one or more containers, e.g., one container per day or per dose (not shown), may be provided to the patient, with each container containing a predetermined amount of DCA, e.g., in powder or other solid or dry form. The container may include a predefined interior volume, e.g., identified by one or more demarcations on the wall of the container, and the predefined volume of water may be added to the container to dissolve the DCA and provide a solution of DCA for oral administration. Optionally, the container may also include a predetermined amount of one or more buffer materials, e.g., sodium hydroxide and/or hydrochloric acid in powder or other solid or dry form, such that the resulting solution has a desired pH, e.g., at least about 7.5. Written instructions may be provided to the patient, e.g., instructing the patient to add the desired amount of water to the container to provide the resulting solution for oral administration.

A patient may take the daily doses over the course of several weeks or months, e.g., until the injured region heals. For example, a region of the patient's vasculature may be injured, e.g., due to balloon expansion during angioplasty and/or stent deployment, and the solution may be administered until the injured microvironment recovers from the injury, e.g., for between about one and twelve (1-12) weeks, between about three and six (3-6) weeks, and the like. In another exemplary embodiment, such DCA solutions may be used to inhibit myointimal hyperplasia in blood vessels or allografts or xenografts, for example, following a coronary bypass graft or other bypass procedure. For example, the solutions may be used to inhibit intimal hyperplasia within a patient's left or right internal mammary artery (IMA) or a allo/xenograft implanted during the bypass procedure. In exemplary embodiments, the allo/xenograft may include a vein harvested from the patient's leg, a radial artery harvested from the patient's arm, and/or other allo/xenografts harvested from the patient or a donor body. Using the DCA solutions and methods described herein, intimal hyperplasia may be inhibited, which may reduce the risk of bypass graft failure.

In yet another embodiment, a kit is provided for inhibiting myointimal hyperplasia that includes a container having a predefined interior volume, and a predetermined mass of DCA within the container, e.g., in powder or other dry form.

When the container is filled to the predefined interior volume with water, the concentration of the DCA within the resulting solution has a desired concentration of DCA for oral administration. In exemplary embodiments, the ratio of the interior volume and mass of DCA may be at least about five hundred milligrams (500 mg) of DCA per kilogram of water, at least about six hundred milligrams (600 mg) of DCA per kilogram of water, at least about seven hundred milligrams (700 mg) of DCA per kilogram of water, or at least about seven hundred fifty milligrams (750 mg) of DCA per kilogram of water. Optionally, the container may also include a predetermined amount of buffer, e.g., a predetermined amount of sodium hydroxide (NaOH) and hydrochloric acid (HCl), such that the resulting solution has a pH of at least 7.5.

Instructions may be provided to the patient to self-administer the DCA solution (or the solution may be administered to the patient by a care provider) based on the weight of the patient. For example, the patient may be instructed to take a daily dose of at least about seventy five milligrams (75 mg) per kilogram of the patient's weight, or at least about one hundred milligrams (100 mg) per kilogram of the patient's weight. For example, a sixty kilogram patient may be provided with a DCA solution having a concentration of about seven hundred fifty milligrams (750 mg) of DCA per kilogram of water and instructed to consume six liters (6 L) of the solution per day to administer about 4,500 mg of DCA (i.e., at about seventy five milligrams per kilogram). Optionally, the DCA solution may be separated into individual doses, e.g., poured into separate smaller containers to facilitate taking the solution multiple times during the course of the day.

Additional information regarding the compositions and methods for use may be found in Appendix A of Ser. No. 62/038,206, incorporated by reference herein.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A method for inhibiting or treating intimal hyperplasia or preventing re-stenosis, comprising:
   providing a solution comprising dichloroacetate (DCA) added to water;
   administering the solution orally to a patient to inhibit or treat intimal hyperplasia or prevent re-stenosis.

2. The method of claim 1, wherein providing a solution comprising DCA comprises:
   providing a predetermined volume of water;
   adding a predetermined amount of DCA to the water; and
   adding one or more buffers to the water to adjust a pH of the solution.

3. The method of claim 1, wherein the concentration of the solution is at least five hundred milligrams (500 mg) of DCA per kilogram of water.

4. The method of claim 1, wherein the concentration of the solution is at least seven hundred fifty milligrams (750 mg) of DCA per kilogram of water.

5. The method of claim 1, wherein the solution is administered to the patient such that the patient receives a daily dose of at least seventy five milligrams (75 mg) per kilogram of the patient's weight.

6. The method of claim 1, wherein the solution is administered to the patient such that the patient receives a daily dose of at least one hundred milligrams (100 mg) per kilogram of the patient's weight.

7. A method for preparing a dichloroacetate (DCA) solution for oral administration to one or more patients for inhibiting or treating intimal hyperplasia, comprising:
   providing a predetermined amount of water;
   adding a predetermined amount of DCA to the water; and
   adding one or more buffers to the water to adjust a pH of the solution.

8. The method of claim 7, wherein the predetermined amount of DCA is in a ratio with the predetermined amount of water of at least seven hundred fifty milligrams (750 mg) of DCA per kilogram of water.

9. A method for inhibiting or treating intimal hyperplasia or preventing re-stenosis in a patient who has undergone a coronary bypass procedure, comprising:
   providing a solution comprising dichloroacetate (DCA) dissolved in water; and
   administering the solution orally to a patient to inhibit or treat intimal hyperplasia or prevent re-stenosis.

10. The method of claim 9, wherein the solution is administered to a patient to inhibit intimal hyperplasia in an internal mammary artery graft.

11. The method of claim 9, wherein the solution is administered to a patient to inhibit intimal hyperplasia in an allograft or xenograft implanted in the patient's body.

12. The method of claim 11, wherein the allograft or xenograft comprises one of a vein harvested from the patient's leg or a radial artery harvested from the patient's arm.

13. The method of claim 9, wherein the wherein the amount of DCA dissolved in the water comprises at least seven hundred fifty milligrams (750 mg) of DCA per kilogram of water.

14. The method of claim 9, wherein the solution is administered to the patient such that the patient receives a daily dose of at least seventy five milligrams (75 mg) per kilogram of the patient's weight.

15. The method of claim 9, wherein the solution is administered to the patient such that the patient receives a daily dose of at least one hundred milligrams (100 mg) per kilogram of the patient's weight.

16. A method for preventing re-stenosis, comprising:
   providing a solution comprising dichloroacetate (DCA) added to water; and
   administering the solution orally to a patient to prevent re-stenosis.

17. The method of claim 16, wherein the solution is administered to the patient to prevent re-stenosis within a blood vessel, graft, or other body structure to reduce the risk of bypass graft failure.

18. The method of claim 16, wherein the solution is administered to the patient to reduce the risk of bypass graft failure in the patient.

* * * * *